(12) United States Patent
Henry et al.

(10) Patent No.: US 11,577,018 B2
(45) Date of Patent: Feb. 14, 2023

(54) BODY CAVITY IRRIGATION INTEGRATED MANUAL CONTROLLER AND PUMP DEVICE, SYSTEM AND METHOD

(71) Applicant: Hollister Incorporated, Libertyville, IL (US)

(72) Inventors: Jerome A. Henry, Castlebar (IE); William K. Arnold, Gurnee, IL (US); Donald V. Matesi, Wauconda, IL (US); Denise Gamblin, Leeds (GB); Mary L. Glennon, Evanston, IL (US); Martin Bruggemann, Mountrath (IE); Colin Conlon, Donadea (IE); Stephen King, Clonlara (IE); Malford E. Cullum, Grayslake, IL (US)

(73) Assignee: Hollister Incorporated, Libertyville, IL (US)

(*) Notice: Subject to any disclaimer, the term of this patent is extended or adjusted under 35 U.S.C. 154(b) by 704 days.

(21) Appl. No.: 16/316,178

(22) PCT Filed: Jul. 7, 2017

(86) PCT No.: PCT/US2017/041127
§ 371 (c)(1),
(2) Date: Jan. 8, 2019

(87) PCT Pub. No.: WO2018/009818
PCT Pub. Date: Jan. 11, 2018

(65) Prior Publication Data
US 2021/0283325 A1 Sep. 16, 2021

Related U.S. Application Data

(60) Provisional application No. 62/359,897, filed on Jul. 8, 2016.

(51) Int. Cl.
*A61M 3/02* (2006.01)

(52) U.S. Cl.
CPC ........ *A61M 3/0262* (2013.01); *A61M 3/0283* (2013.01); *A61M 3/0295* (2013.01);
(Continued)

(58) Field of Classification Search
CPC ................ A61M 39/223; A61M 25/04; A61M 2205/3337; A61M 2205/3331;
(Continued)

(56) References Cited

U.S. PATENT DOCUMENTS

| 1,004,103 | A | 9/1911 | Tacey |
| 1,286,083 | A | 11/1918 | Pennington |

(Continued)

FOREIGN PATENT DOCUMENTS

| CN | 105999453 A | * 10/2016 |
| CN | 105999454 A | * 10/2016 |

(Continued)

OTHER PUBLICATIONS

International Search Report of the International Search Authority for PCT Application No. PCT/US2017/041127, dated Nov. 13, 2017.

(Continued)

*Primary Examiner* — Jason E Flick
*Assistant Examiner* — Adam J. Cermak
(74) *Attorney, Agent, or Firm* — Cook Alex Ltd.

(57) ABSTRACT

A system for performing irrigation of a body cavity includes a reservoir containing an irrigation liquid, a catheter and a controller. The catheter is configured to be at least partially inserted into the body cavity and has a flushing passage, a drain passage and a retention balloon. A waste drain valve is in fluid communication with the drain passage of the catheter and is movable between a closed configuration, where (Continued)

waste is retained within the drain passage, and an open configuration where waste flows through the drain passage. The controller is in fluid communication with the reservoir and the catheter, and has a pump and a valve assembly. The valve assembly is changeable between configurations where, when the pump is actuated, irrigation liquid is pumped from the reservoir to the retention balloon, from the reservoir to the flushing passage of the catheter and from the retention balloon to the reservoir.

11 Claims, 29 Drawing Sheets

(52) U.S. Cl.
CPC ............... *A61M 2205/3337* (2013.01); *A61M 2210/1067* (2013.01)

(58) Field of Classification Search
CPC .. A61M 2210/1067; A61M 2210/1064; A61M 2210/105; A61M 3/0295; A61M 3/0208; A61M 3/0262; A61M 3/0279; A61M 3/022; A61M 3/0283; A61M 3/0254; F16K 17/0406; F16K 11/074; F16K 5/18; F16K 5/0414; F16K 31/53; F16K 31/535; F16K 31/54; F16K 15/184; F16K 15/1848; F16K 15/188; F16K 5/181; F16K 5/182; F16K 5/184; F16K 5/185; F16K 5/187; F16K 5/188; F15B 13/0406; Y10T 137/877; Y10T 137/87788; Y10T 137/87804; Y10T 137/87708; Y10T 137/86823; Y10T 137/87732; Y10T 137/8782; Y10S 128/12
USPC ........ 604/514, 132, 19, 27, 36, 37; 251/208, 251/309, 248–250.5; 137/865, 876
See application file for complete search history.

(56) References Cited

U.S. PATENT DOCUMENTS

| | | | |
|---|---|---|---|
| 1,470,699 A * | 10/1923 | Olsen | F16K 11/0743 |
| | | | 137/625.15 |
| 1,710,701 A | 4/1929 | Hertzberg | |
| 1,853,202 A | 4/1932 | Catlin | |
| 2,691,373 A * | 10/1954 | Bried | A61M 3/0233 |
| | | | 604/265 |
| 3,042,039 A * | 7/1962 | Dahlstrom | A61M 3/0225 |
| | | | 604/30 |
| 3,489,389 A * | 1/1970 | Kaatz | F16K 5/184 |
| | | | 251/163 |
| 3,653,377 A | 4/1972 | Rebold | |
| 3,731,676 A | 5/1973 | Rebold | |
| 3,794,031 A | 2/1974 | Bloom | |
| 3,802,418 A | 4/1974 | Clayton | |
| 3,910,274 A | 10/1975 | Nolan | |
| 4,117,847 A | 10/1978 | Clayton | |
| 4,457,488 A * | 7/1984 | Ishii | F16K 5/188 |
| | | | 251/129.11 |
| 4,682,979 A | 7/1987 | Girouard | |
| 4,890,340 A | 1/1990 | Lovitt | |
| 4,904,245 A * | 2/1990 | Chen | A61M 3/0233 |
| | | | 137/625.47 |
| 5,004,005 A * | 4/1991 | Graves | F16K 15/1848 |
| | | | 137/269.5 |
| 5,019,054 A * | 5/1991 | Clement | A61B 18/1482 |
| | | | 604/248 |
| 5,097,540 A | 3/1992 | Lovitt | |
| 5,113,906 A * | 5/1992 | Hogner | F16K 7/065 |
| | | | 137/595 |
| 5,176,630 A | 1/1993 | Shilling et al. | |
| 5,190,519 A | 3/1993 | Mead et al. | |
| 5,405,319 A * | 4/1995 | Abell | A61M 3/0208 |
| | | | 604/27 |
| 5,443,445 A | 8/1995 | Peters et al. | |
| 5,864,895 A | 2/1999 | Ota et al. | |
| 5,871,463 A * | 2/1999 | Baker | A61M 3/025 |
| | | | 604/27 |
| 6,106,506 A | 8/2000 | Abell et al. | |
| 6,125,843 A | 10/2000 | Gold et al. | |
| 6,468,245 B2 | 10/2002 | Alexandersen | |
| 6,751,813 B2 | 6/2004 | Chung | |
| 6,761,702 B2 | 7/2004 | Smith | |
| 6,984,226 B1 | 1/2006 | Abell et al. | |
| 7,147,627 B2 | 12/2006 | Kim et al. | |
| 7,914,505 B2 | 3/2011 | Moeller-Jensen et al. | |
| 8,231,589 B2 | 7/2012 | Moeller-Jensen et al. | |
| 8,292,857 B2 * | 10/2012 | Martini | A61M 1/0001 |
| | | | 604/317 |
| 8,518,012 B2 | 8/2013 | Smith | |
| 8,568,348 B2 | 10/2013 | Vlodaver et al. | |
| 8,574,206 B2 | 11/2013 | Bjerregaard et al. | |
| 8,579,850 B2 | 11/2013 | Bjerregaard | |
| 8,657,801 B2 | 2/2014 | Nielsen et al. | |
| 8,905,981 B2 * | 12/2014 | Budig | A61M 39/223 |
| | | | 604/275 |
| 10,610,636 B2 * | 4/2020 | Zhou | A61M 3/025 |
| 2003/0073974 A1 * | 4/2003 | Falconer | A61M 3/0262 |
| | | | 604/514 |
| 2004/0260152 A1 | 12/2004 | Sant et al. | |
| 2005/0070933 A1 | 3/2005 | Leiboff | |
| 2005/0148954 A1 | 7/2005 | Abell | |
| 2005/0277811 A1 | 12/2005 | Richards et al. | |
| 2006/0009732 A1 * | 1/2006 | Hardy | A61M 3/0275 |
| | | | 604/35 |
| 2006/0025728 A1 | 2/2006 | Leiboff et al. | |
| 2006/0025729 A1 * | 2/2006 | Leiboff | A61M 3/0208 |
| | | | 604/317 |
| 2006/0129135 A1 * | 6/2006 | Moeller-Jensen | A61M 3/0262 |
| | | | 604/540 |
| 2007/0073216 A1 * | 3/2007 | McAuliffe | A61M 31/00 |
| | | | 604/30 |
| 2008/0065001 A1 | 3/2008 | DiNucci et al. | |
| 2008/0135794 A1 * | 6/2008 | Shnider | B60R 25/08 |
| | | | 251/315.1 |
| 2010/0249752 A1 | 9/2010 | Tanghoej | |
| 2011/0060199 A1 * | 3/2011 | Robinson | A61B 5/15003 |
| | | | 600/316 |
| 2011/0144588 A1 | 6/2011 | Taylor et al. | |
| 2011/0282311 A1 | 11/2011 | Nishtala | |
| 2011/0295236 A1 | 12/2011 | Gregory | |
| 2011/0302709 A1 | 12/2011 | Taylor et al. | |
| 2012/0080102 A1 * | 4/2012 | Kee | F16K 3/08 |
| | | | 137/493.8 |
| 2013/0237920 A1 | 9/2013 | Kokenis | |
| 2013/0245380 A1 | 9/2013 | Vogel | |
| 2013/0331781 A1 | 12/2013 | Andreen | |
| 2014/0005602 A1 | 1/2014 | Andreen et al. | |
| 2014/0121515 A1 * | 5/2014 | Vitullo | A61M 25/10185 |
| | | | 600/435 |
| 2014/0155864 A1 | 6/2014 | Andreen | |
| 2014/0276631 A1 | 9/2014 | Gilman | |
| 2015/0088055 A1 * | 3/2015 | Tan | A61M 1/3661 |
| | | | 604/33 |
| 2016/0339166 A1 * | 11/2016 | Adam | A61M 3/0258 |
| 2020/0088311 A1 * | 3/2020 | Hertenberger | F16K 5/10 |

FOREIGN PATENT DOCUMENTS

| | | | | |
|---|---|---|---|---|
| DE | 4114390 | A1 * | 11/1992 | ........ A61M 3/0279 |
| DE | 4332221 | A1 * | 3/1995 | ........ F16K 15/188 |
| DE | 29805247 | U1 * | 6/1998 | ........ F16K 5/0605 |
| DE | 102017108645 | A1 * | 10/2018 | ........ F15B 13/0406 |
| EP | 1051984 | | 11/2000 | |
| EP | 1491223 | | 12/2004 | |
| EP | 1716876 | A1 * | 11/2006 | ........ F16K 24/046 |
| EP | 1752177 | | 2/2007 | |
| EP | 1946785 | | 7/2008 | |
| EP | 1977778 | | 10/2008 | |

(56) References Cited

FOREIGN PATENT DOCUMENTS

| | | | | |
|---|---|---|---|---|
| EP | 2005981 | 12/2008 | | |
| EP | 2027832 | 2/2009 | | |
| EP | 2158926 | 3/2010 | | |
| EP | 2452706 | 5/2012 | | |
| EP | 2468326 | 6/2012 | | |
| EP | 2671602 A1 | 12/2013 | | |
| EP | 2679259 | 1/2014 | | |
| EP | 2679260 | 1/2014 | | |
| EP | 2679261 | 1/2014 | | |
| EP | 2703019 | 3/2014 | | |
| GB | 2496900 | 5/2013 | | |
| JP | 58128576 A | * | 8/1983 | ........... F16K 5/0605 |
| JP | 58128577 A | * | 8/1983 | ........... F16K 5/0605 |
| KR | 20150071021 A | * | 6/2015 | ........... A61M 5/1408 |
| WO | WO1987001596 | 3/1987 | | |
| WO | WO9625188 | 8/1996 | | |
| WO | WO9631250 | 10/1996 | | |
| WO | WO9715335 | 5/1997 | | |
| WO | WO9749441 | 12/1997 | | |
| WO | WO9820722 | 5/1998 | | |
| WO | WO9823312 | 6/1998 | | |
| WO | WO9930652 | 6/1999 | | |
| WO | WO9959656 | 11/1999 | | |
| WO | WO0149345 | 7/2001 | | |
| WO | WO0207668 | 1/2002 | | |
| WO | WO2002013887 | 2/2002 | | |
| WO | WO02074363 | 9/2002 | | |
| WO | WO03030967 | 4/2003 | | |
| WO | WO03030968 | 4/2003 | | |
| WO | WO03063668 | 8/2003 | | |
| WO | WO2004060259 | 7/2004 | | |
| WO | WO2004112712 | 12/2004 | | |
| WO | WO2005032617 | 4/2005 | | |
| WO | WO-2005042059 A2 | * | 5/2005 | ........... A61M 1/367 |
| WO | WO2006010556 | 2/2006 | | |
| WO | WO2006024205 | 3/2006 | | |
| WO | WO2006135934 | 12/2006 | | |
| WO | WO2007103995 | 9/2007 | | |
| WO | WO2008048856 | 4/2008 | | |
| WO | WO2008058160 | 5/2008 | | |
| WO | WO2008087220 | 7/2008 | | |
| WO | WO2008087221 | 7/2008 | | |
| WO | WO2009015152 | 1/2009 | | |
| WO | WO2009056906 | 5/2009 | | |
| WO | WO2009128109 | 10/2009 | | |
| WO | WO2009144028 | 12/2009 | | |
| WO | WO2009153973 | 12/2009 | | |
| WO | WO-2010039662 A2 | * | 4/2010 | ........... A61M 39/223 |
| WO | WO2010047501 | 4/2010 | | |
| WO | WO-2010057208 A1 | * | 5/2010 | ........... A61F 5/4405 |
| WO | WO2010077980 | 7/2010 | | |
| WO | WO2010115430 | 10/2010 | | |
| WO | WO-2010115431 A2 | * | 10/2010 | ........... A61M 3/0262 |
| WO | WO2010126586 | 11/2010 | | |
| WO | WO2011012323 | 2/2011 | | |
| WO | WO2011075581 | 6/2011 | | |
| WO | WO2011105644 | 9/2011 | | |
| WO | WO2011139498 | 11/2011 | | |
| WO | 2012120456 A2 | 9/2012 | | |
| WO | WO2012164559 | 12/2012 | | |
| WO | WO2013026564 | 2/2013 | | |
| WO | WO2013026565 | 2/2013 | | |
| WO | WO2013076446 | 5/2013 | | |
| WO | WO2013090778 | 6/2013 | | |
| WO | WO2013163364 | 10/2013 | | |
| WO | WO2013184158 | 12/2013 | | |
| WO | WO2014001292 | 1/2014 | | |
| WO | WO2014001313 | 1/2014 | | |
| WO | WO2014001322 | 1/2014 | | |
| WO | WO2014064414 | 5/2014 | | |
| WO | WO2014089278 | 6/2014 | | |
| WO | 2015031851 A2 | 3/2015 | | |
| WO | WO-2015031851 A2 | * | 3/2015 | ........... A61M 3/0262 |
| WO | WO2015117141 | 8/2015 | | |
| WO | WO-2015163181 A1 | * | 10/2015 | ............... F01P 3/18 |
| WO | 2016007536 A1 | 1/2016 | | |
| WO | WO-2016007536 A1 | * | 1/2016 | ........... A61M 3/0287 |
| WO | 2016095928 A1 | 6/2016 | | |
| WO | WO-2016095929 A1 | * | 6/2016 | ............. A61F 5/442 |
| WO | WO-2017016306 A1 | * | 2/2017 | ........... A61M 3/0216 |

OTHER PUBLICATIONS

Invitation to Pay Additional Fees with Provisional Opinion of the International Search Authority for PCT Application No. PCT/US2017/041127, dated Sep. 21, 2017.

McWilliams, D.. "Rectal irrigation for patients with functional bowel disorders." Nursing standard (Royal College of Nursing (Great Britain) : 1987) 24 26 (2010): 42-7.

Peristeen—Anal irrigation—My Bowel, Coloplast, Website: my-bowel-.co.uk, dated Jan. 18, 2016.

Popolo, G. et al. "Treatment of neurogenic bowel dysfunction using transanal irrigation: a muiticenter Italian study." Spinal Cord 46 (2008): 517-522.

International Search Report and Written Opinion Issued by the International Search Authority for International Application No. PCT/US2017/041127, dated Nov. 13, 2017 (18 pages).

Extended European Search Report dated Apr. 29, 2021 from EP21161727.9.

* cited by examiner

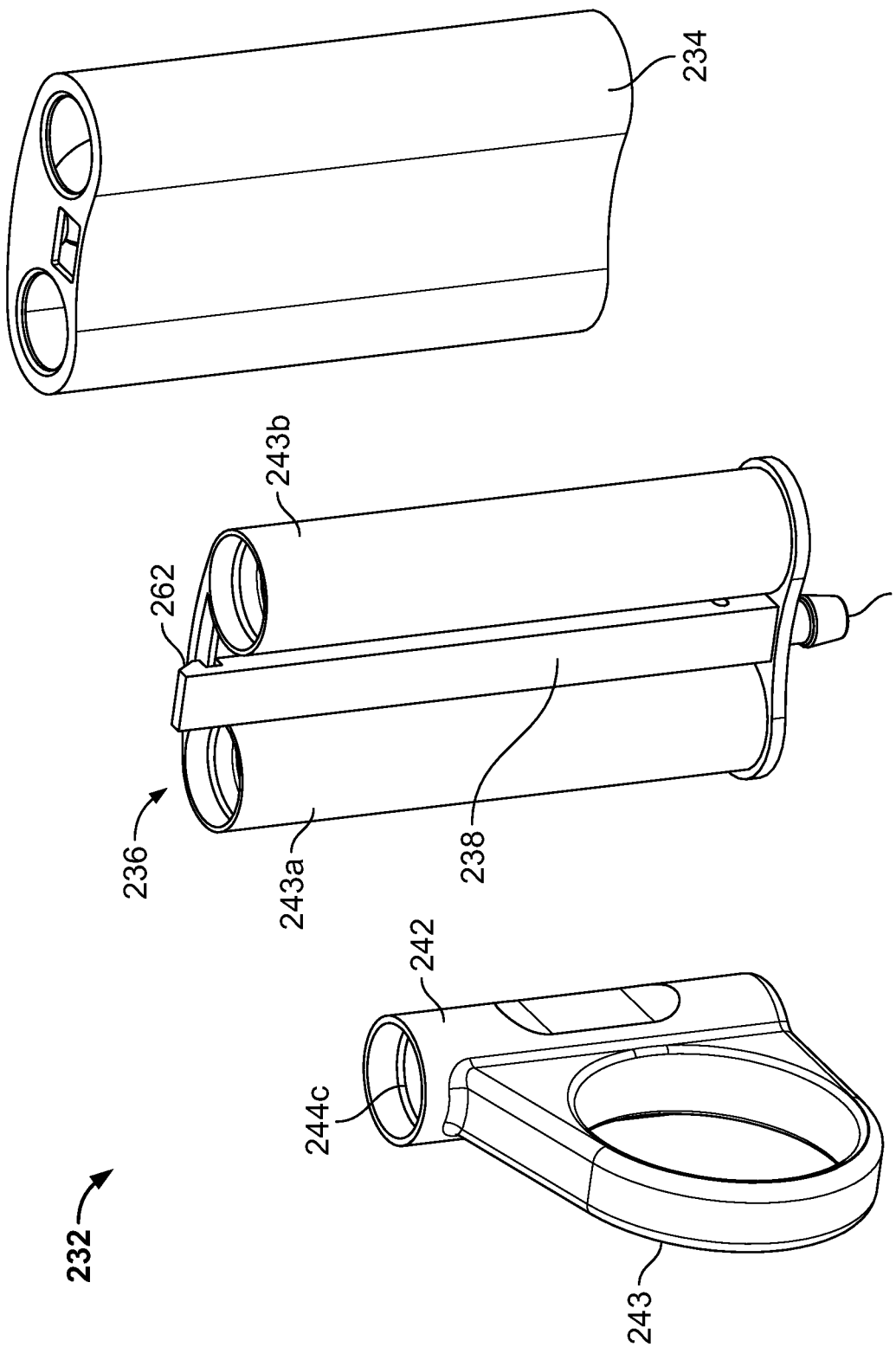

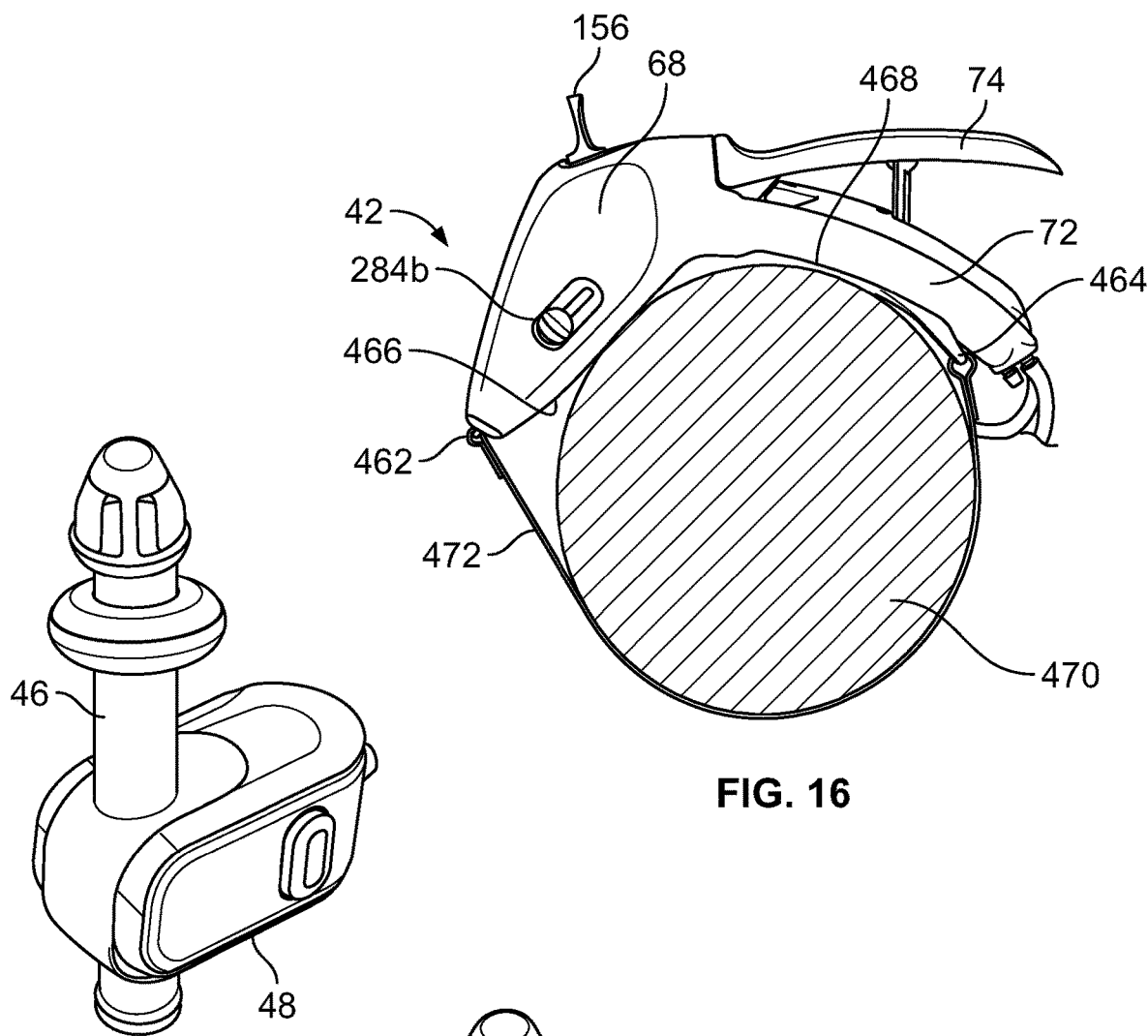
FIG. 16
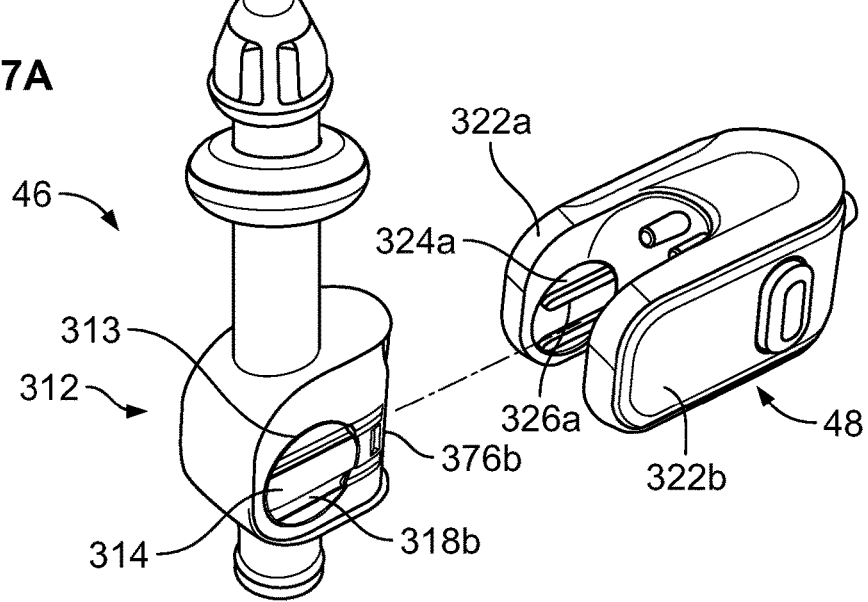
FIG. 17A
FIG. 17B

| Wheel Icon | Valve 1<br>Reservoir↔Pump<br>(116c) | Valve 2<br>Pump↔Catheter<br>(116a) | Valve 3<br>Pump↔Balloon<br>(116b) | Waste Valve<br>313 |
|---|---|---|---|---|
| Prime | | | | |
| Balloon Inflate | | | | |
| Irrigate | | | | |
| Flush | | | | |
| Balloon Deflate | | | | |
| Off | | | | |

FIG. 27

BODY CAVITY IRRIGATION INTEGRATED MANUAL CONTROLLER AND PUMP DEVICE, SYSTEM AND METHOD

RELATED APPLICATIONS

This application is the U.S. National Stage of PCT International Patent Application No. PCT/US2017/41127, filed Jul. 7, 2017, which claims the benefit of and priority of U.S. Provisional Patent Application Ser. No. 62/359,897, filed Jul. 8, 2016, the contents of both of which are incorporated by reference herein.

FIELD OF THE INVENTION

The present disclosure relates generally to body cavity irrigation devices, methods and systems and, in particular, to a body cavity irrigation integrated manual controller and pump device, system and method.

BACKGROUND

Transanal irrigation (TAI) is a process used by individuals who have bowel management issues, such as incontinence, constipation or other neurogenic bowel dysfunction (NBD). Alternatively, TAI may be used for regular bowel evacuations by individuals who are incapacitated due to illness or other medical conditions or injuries (such as spinal cord injury) and thus lack the mobility to access a toilet. During TAI, water or other lavage liquid is introduced into the rectum and colon through a device positioned through the anus so that feces are flushed and evacuated. This creates pseudo-continence for the patient/user. Furthermore, individuals that are bedridden may develop fecal impaction. Such bowel obstructions may be removed via TAI.

Systems for performing TAI currently on the market allow the user to introduce water into the bowel through a rectal catheter while the user sits on a toilet or a commode/shower chair or lays in a bed. The user introduces an amount of water or other liquid into the bowel (typically 500-700 mL) in order to flush out stool located in the bowel passage. The user typically introduces the water, waits for a period of time and then allows gravity to flush the water and stool out of the body. The rectal catheter may have an inflatable/deflatable balloon to assist in retention of the catheter during water introduction. The balloon is typically inflated by a fluid such as air or water.

For TAI users, independence, dexterity, and ease of use are important needs that must be addressed by a TAI system or method.

A prior art TAI device is shown in U.S. Pat. No. 8,579,850 to Bjerregaard and uses water to inflate the balloon of a rectal catheter. This system has single-lumen tubing that provides water from a reservoir to a controller. The system features dual-lumen tubing from the controller to the catheter. One of these dual lumens enables the rectal catheter balloon to be inflated with water from the reservoir and later deflated; while the second lumen accommodates water transfer from the reservoir into the rectum. When the catheter balloon is deflated, a liquid communication channel is created so that water returning from the deflated balloon travels via the controller into the lumen towards the catheter, and thus into the rectum. As a result, the water from the deflated balloon does not return to the water reservoir. A disadvantage of such a system is that water from the balloon is unnecessarily directed into the patient.

Prior art systems that use controllers with built-in valves to selectively direct fluids to a flushing catheter and an inflation balloon are also known. Examples of such systems are presented by the Bjerregaard '850 patent and U.S. Pat. No. 8,657,801 to Nielsen et al. Such controllers, however, use rotating knobs to select the controller valve configuration, which can be difficult for a patient/user to manipulate. As a result, it is all too easy for a user/patient to select the wrong valve setting.

Furthermore, prior art manual pump TAI systems, such as the systems of the Bjerregaard '850 patent and the Nielsen et al. '801 patent, use a squeeze bulb to pump fluids. As a result, the user/patient must hold the squeeze bulb in addition to squeezing it to activate the pumping action. This can be awkward for a patient/user and may result in inadequate pumping pressure.

In addition, the catheters of the Bjerregaard '850 patent and the Nielsen et al. '801 patent must be removed for flushed stool and lavage liquid to drain. This requires the catheter to be reinserted into the anus if multiple flushing cycles are to be repeated.

Accordingly is a desire to develop a TAI controller and pump device, system and/or method for bowel management that addresses at least some of the above issues.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a system for performing irrigation of a body cavity includes a reservoir configured to contain an irrigation liquid, a controller and a catheter configured to be at least partially inserted into the body cavity having a flushing passage, a drain passage and a retention balloon. A waste drain valve is in fluid communication with the drain passage of the catheter and movable between a closed configuration, where waste is retained within the drain passage, and an open configuration where waste flows through the drain passage. The controller is in fluid communication with the reservoir and the catheter and has a pump and a valve assembly. The valve assembly is changeable between configurations where, when the pump is actuated: i) irrigation liquid is pumped from the reservoir to the retention balloon; ii) irrigation liquid is pumped from the reservoir to the flushing passage of the catheter; and iii) irrigation liquid is pumped from the retention balloon to the reservoir.

In another aspect, a method for irrigating a body cavity includes providing a catheter having a waste drain valve, a flushing port and a retention balloon, a reservoir containing irrigation liquid and a controller including a pump in fluid communication with the reservoir and the catheter. A portion of the catheter including the retention balloon is inserted into the body cavity. The waste drain valve of the catheter is closed and irrigation liquid from the reservoir is pumped to the retention balloon using the controller so that the retention balloon is inflated. Irrigation liquid from the reservoir is then pumped to the flushing port of the catheter so that the irrigation liquid enters the body cavity. The waste drain valve of the catheter is opened so that liquefied waste is drained from the body cavity. Liquid is pumped from the retention balloon to the reservoir so that the retention balloon is deflated. The catheter is removed from the body cavity.

In yet another aspect, a device for irrigating a body cavity using irrigation liquid from a reservoir and a catheter having a flushing port and a retention balloon includes a pump and a valve assembly in fluid communication with the pump. The valve assembly is changeable between configurations where, when the pump is actuated: i) irrigation liquid is pumped from the reservoir to the retention balloon; ii) irrigation liquid is pumped from the reservoir to the flushing passage of the catheter; and iii) irrigation liquid is pumped from the retention balloon to the reservoir.

In yet another aspect, a device for controlling a flow of irrigation liquid between a catheter and a reservoir for use in flushing a body cavity of a user includes a housing and a valve positioned in the housing and movable between a first configuration and a second configuration. A gear train shaft is rotatably positioned within the housing and a valve gear is mounted on the gear train shaft. The valve gear engages the valve to move it between the first configuration and the second configuration when the gear train shaft is rotated. A ratchet wheel is also mounted on the gear train shaft and a toggle switch is slidably mounted on the housing. A pawl is connected to the toggle switch and engages the ratchet wheel so as to turn the ratchet wheel and shaft when the toggle switch is slid.

BRIEF DESCRIPTION OF THE DRAWINGS

FIGS. 15A and 15B are enlarged perspective views of the tubing and drain valve line connector of FIG. 14 with the drain valve line slider in the rest and actuated positions, respectively;

FIG. 16 is a cross sectional view of a user's leg with the controller of FIG. 1 attached thereto;

FIGS. 17A and 17B are perspective views of the catheter and hub of FIG. 1 in the connected and disconnected configurations, respectively;

FIG. 27 is a schematic view of the controller valve configurations and corresponding symbols of the indicator wheel of the toggle mechanism;

DETAILED DESCRIPTION OF EMBODIMENTS

Figure 1:
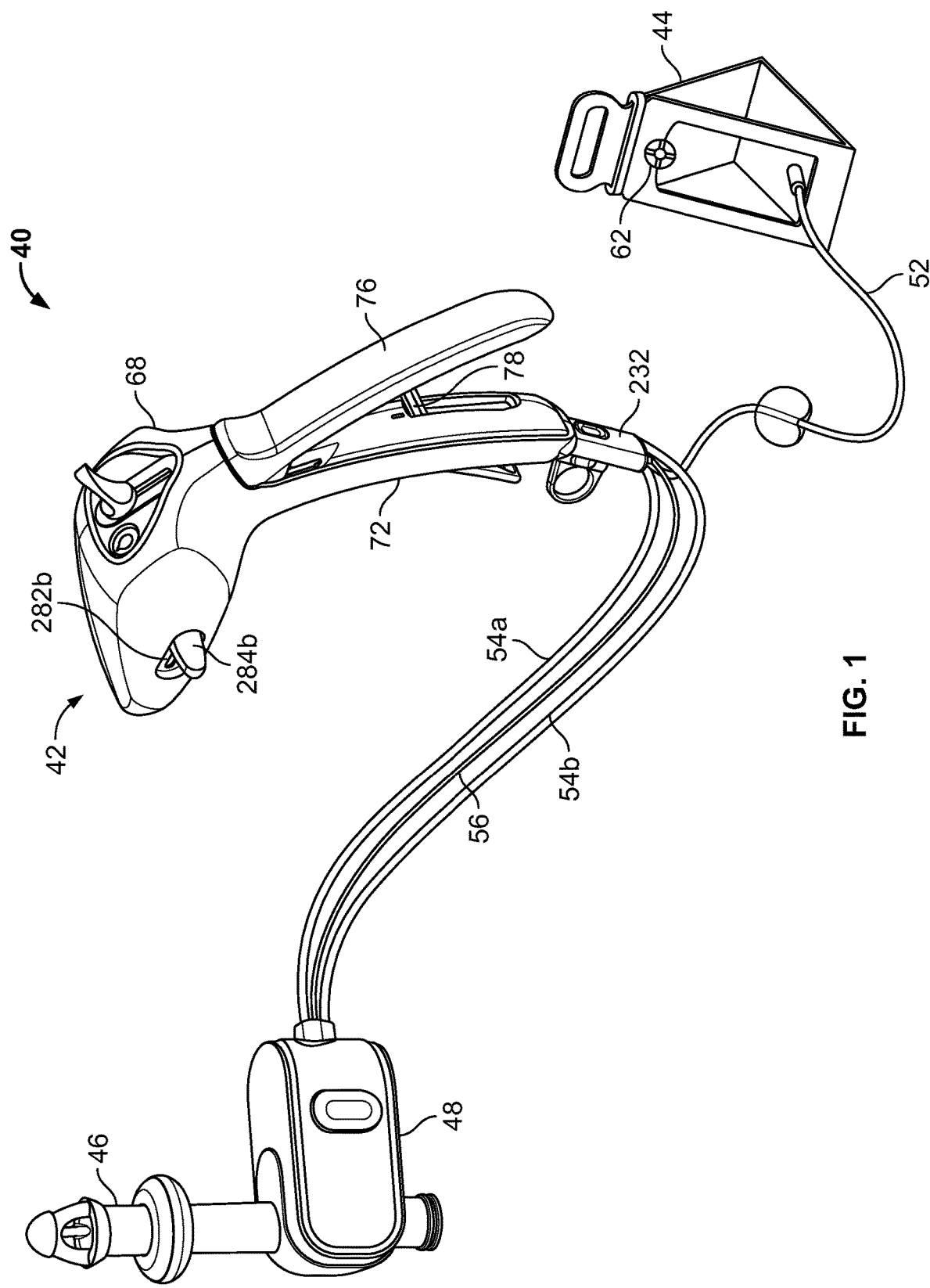
FIG. 1 is a perspective view of an embodiment of the system of the present invention.

An embodiment of the transanal irrigation (TAI) system of the invention is indicated in general at 40 in FIG. 1. The system includes an integrated pump controller, indicated in general at 42, an irrigant or lavage liquid reservoir 44, a rectal catheter 46 and a catheter hub 48. A single section of tubing 52 runs between the reservoir and the controller. A pair of tubing sections 54*a* and 54*b* run from the controller to the catheter base 48. In the embodiment of FIG. 1, the lumens of tubing sections 54*a* and 54*b* are never placed in communication with each other during a TAI procedure, i.e. there is no fluid communication between the lumens. As will be explained in greater detail below, this is accomplished since each tubing lumen is controlled independently by its own unique valve.

While the invention is described below in terms of use in a transanal irrigation procedure, it is to be understood that the invention could be used to irrigate other body cavities of a user including, but not limited to, stomas and body cavities accessible by stomas.

A sheath 56 containing a waste drain valve line also runs between the controller 42 and the catheter hub 48.

The rectal catheter 46 preferably is disposable and is attached in a removable fashion to (non-disposable) hub 48. The rectal catheter 46 may be used by a patient either on a toilet or the like or in a bed setting.

Figure 2:
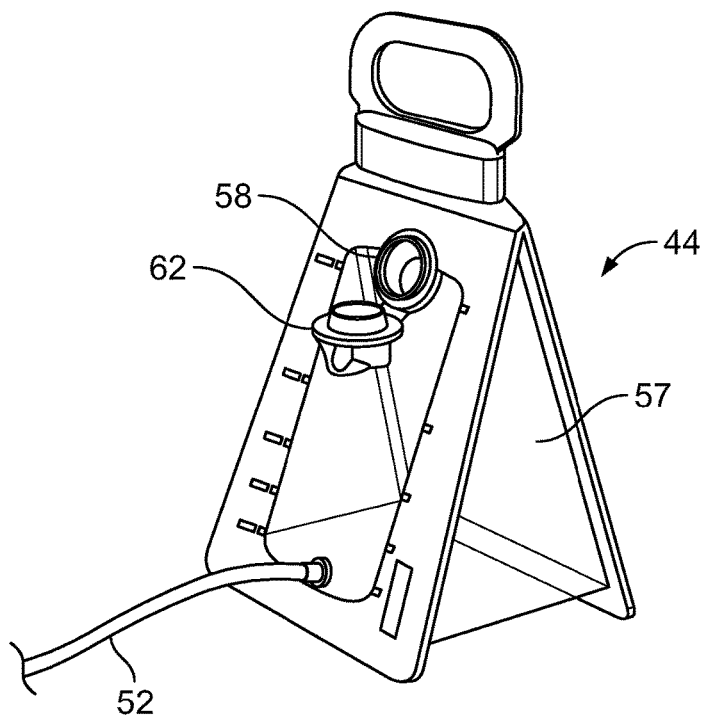
FIG. 2 is an enlarged perspective view of the reservoir of FIG. 1 with the fill cap removed, empty of liquid and ready for filling.
Figure 3:
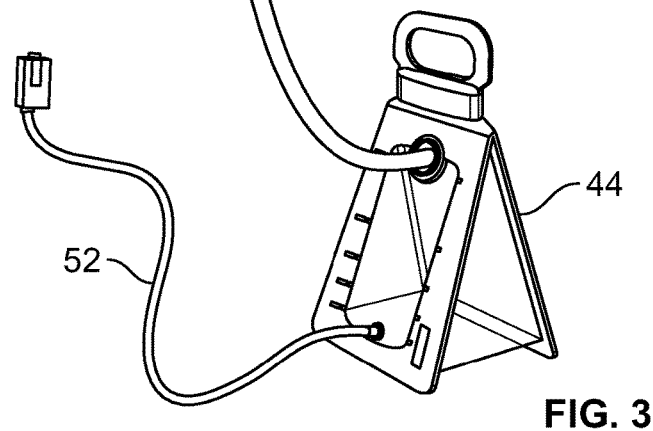
FIG. 3 shows the reservoir of FIG. 2 configured to be filled with water.

As illustrated in FIG. 2, the reservoir 44 houses a liquid tank or container 57 and features a fill opening 58 with a removable fill cap 62. As illustrated in FIG. 3, with the fill cap removed, the container of the reservoir may be refilled with lavage liquid by a hose 64 that receives a liquid, such as water, from a water source 66.

Figure 4:
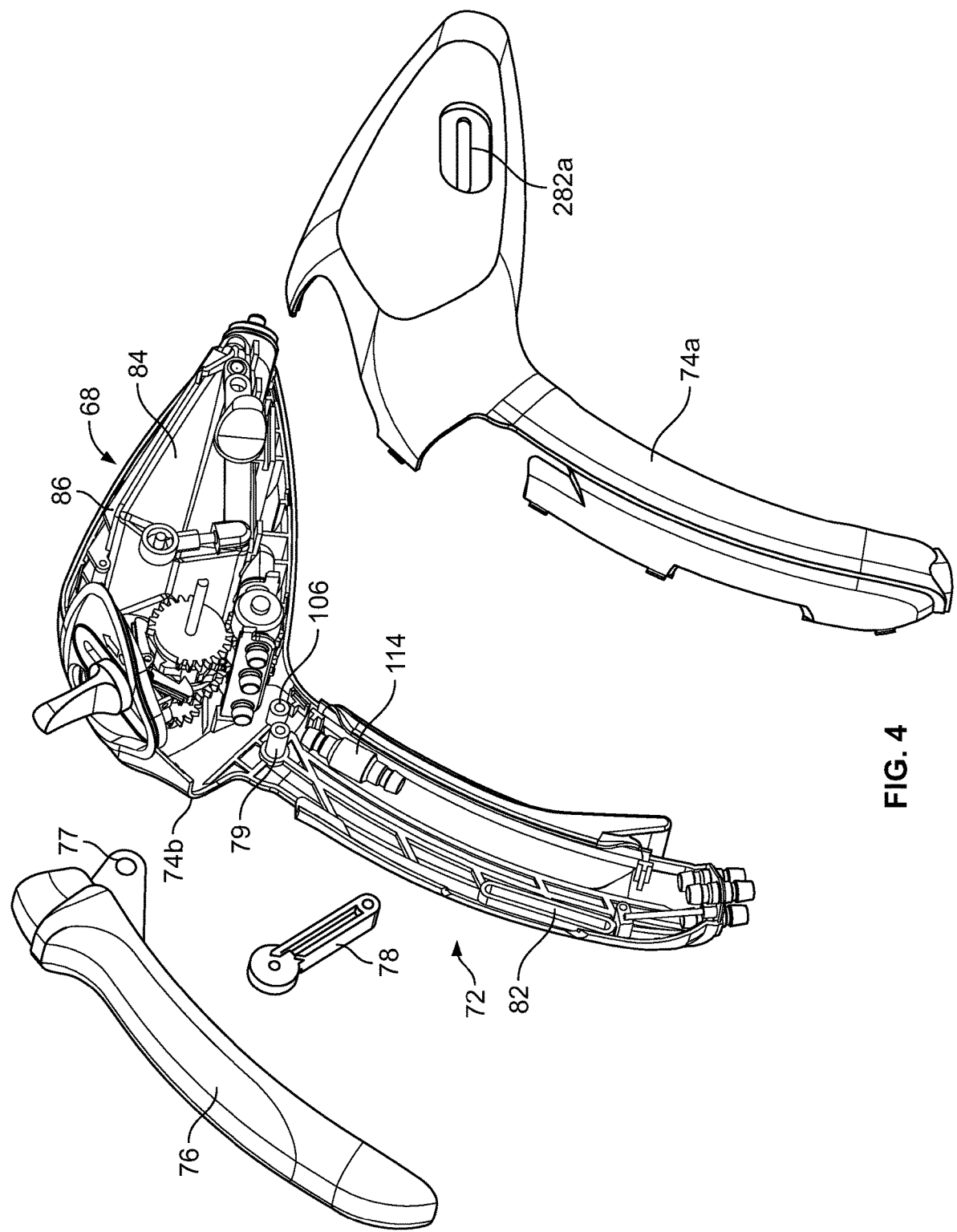
FIG. 4 is an enlarged exploded perspective view of the housing, pumping handle and the controller of FIG. 1.

With reference to FIGS. 1 and 4, the controller 42 includes a housing that forms a head portion 68 and a handle portion 72. The housing is formed by halves 74a and 74b. As will be explained in greater detail below, the head portion houses the controller valve assembly and associated toggle mechanism for selecting the controller valve configuration, the pump bellows and the sliding catheter drain valve switches. Controller connector ports are positioned on the bottom end of the handle portion, which also houses the internal tubing that runs between the valve assembly and connector ports as well as an internal control line for the catheter drain valve switches.

As shown in FIGS. 1 and 4, a pumping lever 76 is pivotally attached by its proximal end (via opening 77 of FIG. 4) to the handle portion of the controller (via boss 79 of FIG. 4). A link 78 is pivotally attached by one end to the underside of the handle 76, while the opposite end of the link traverses grooves 82 (FIG. 4) formed in housing halves 74a and 74b as the handle 76 is actuated during pumping.

Figure 5:
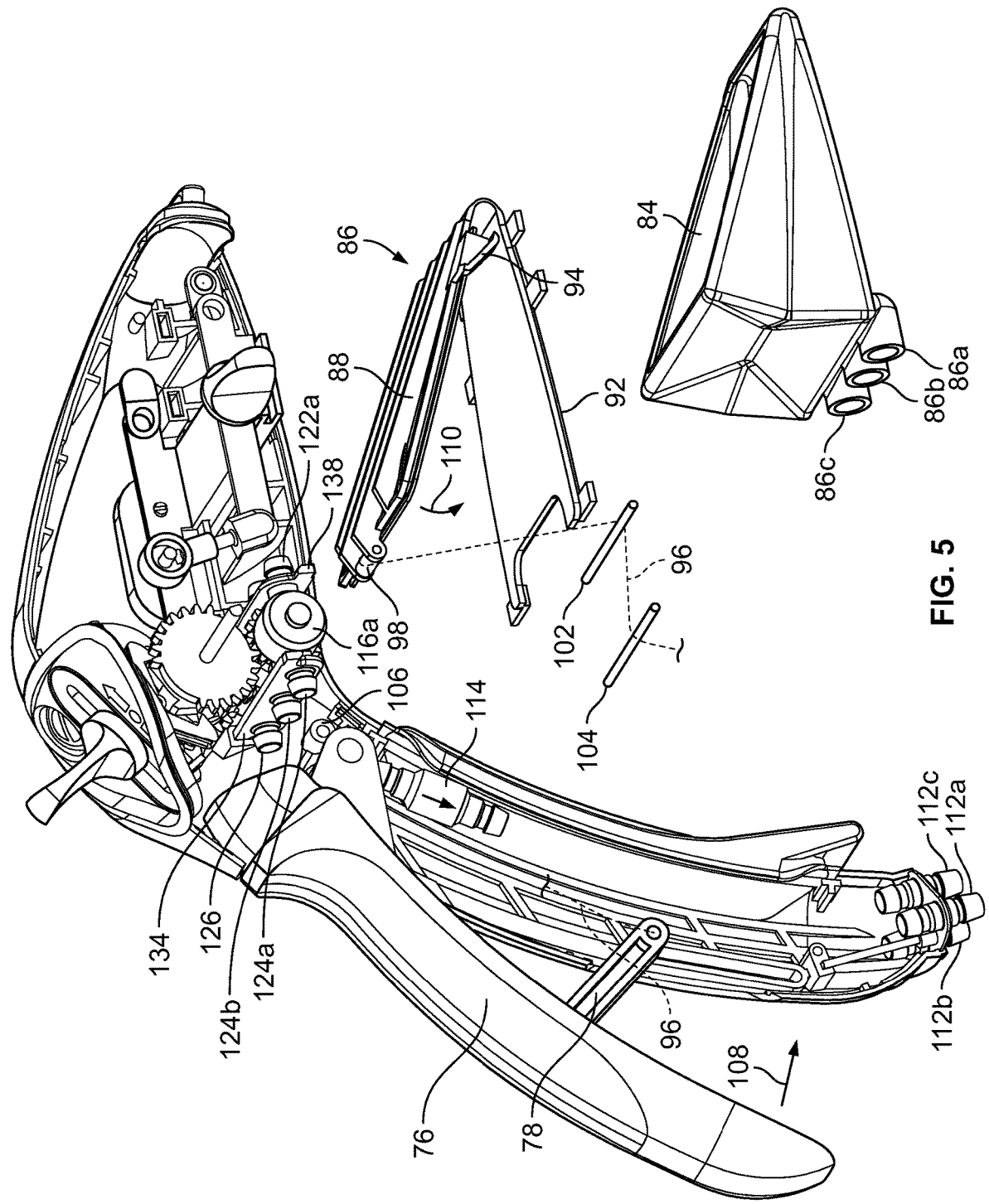
FIG. 5 is an exploded view of the pumping bellows assembly of the controller of FIG. 4.

As shown in FIGS. 4 and 5, a pumping bellows assembly is mounted in the head portion of the controller and includes a bellows 84 that contains an interior pumping chamber. The bellows is provided with ports 86a, 86b and 86c that communicate with the interior pumping chamber. The bellows 84 may be constructed from rubber or any other liquid impermeable material that is at least semi-flexible.

The bellows 84 is mounted within a pumping bellows frame 86 that features top and bottom plates 88 and 92 that are joined by their leading edges by a hinge arrangement. As an example only, the plates 88 and 92 may be integrally formed of plastic and joined by a living hinge. A spring tab 94 is formed on upper plate 88 and features a distal end that engages lower plate 92 so as to urge the plates into the positions shown in FIG. 5. The top and bottom surfaces of the bellows 84 are attached to the plates 88 and 92, respectively, such as by adhesive, and thus the bellows is urged into the expanded configuration illustrated in FIG. 5.

As illustrated in phantom at 96 in FIG. 5, a first end of a line is attached to plate 88 at line mounting bracket 98 and runs below pin 102 and over pin 104 that extend between the housing halves. The second end of the line is connected to the sliding end of link 78. While pins 102 and 104 are shown outside of the controller housing for ease of illustration, pin 104 extends between boss 106 (FIGS. 4 and 5) in housing half 74b and a corresponding boss formed in housing half 74a. Pin 102 is similarly mounted between the controller housing halves, but in a position within the head portion of the controller below the bellows assembly and generally in vertical alignment with the line mounting bracket 98.

In operation, when lever 76 is squeezed by the user towards the handle portion of the controller housing (as illustrated by arrow 108 of FIG. 5), the line 96 is pulled downward by the sliding end of link 78 so that the top plate 88 of the bellows frame is moved towards the bottom plate (as illustrated by arrow 110) against the urging of spring tab 94. This moves the bellows 84 into the contracted or compressed configuration so that liquid within it is pushed out of the bellows. When the lever 76 is released by the user, spring tab 94 moves the top plate 88 of the bellows frame away from bottom plate 92 so that the bellows is moved into the expanded configuration (of FIG. 5). As a result, liquid is drawn into the bellows. The source of liquid drawn into the bellows and the destination of the liquid pushed out of the bellows is dictated by the setting of the controller valves, as will be described below.

As shown in FIG. 5, the bottom of the handle portion of the controller is provided with controller connector ports 112a, 112b and 112c. Port 112a is connected to tubing 54a of FIG. 1, port 112b is connected to tubing 54b of FIG. 1 and port 112c is connected to tubing 52 of FIG. 1. Internal tubing (not shown) runs between port 112a and the outlet of a fixed check valve 114.

Figure 6:
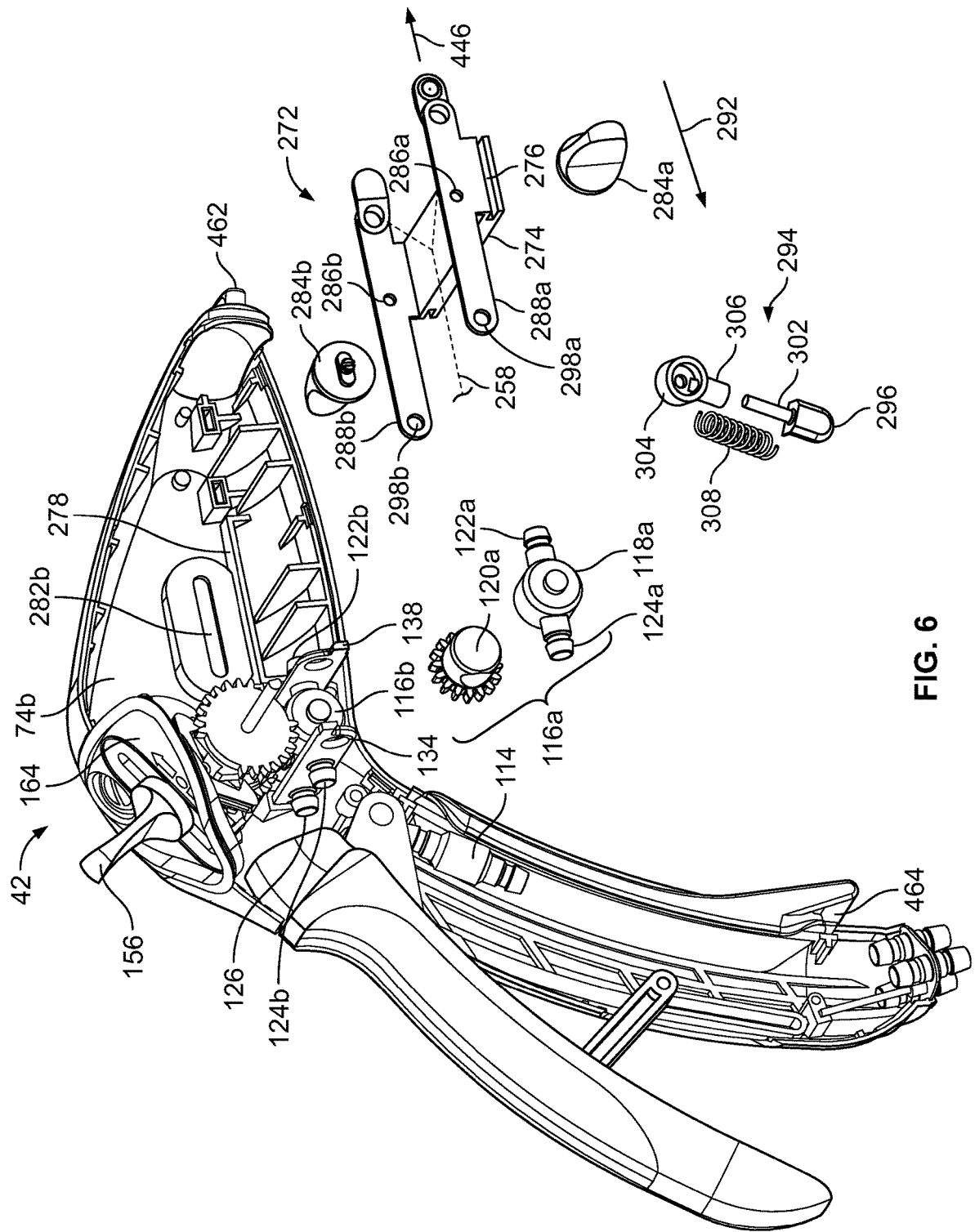
FIG. 6 is an exploded view of the catheter waste drain valve switch carriage assembly and one of the valves of the controller of FIG. 4.
Figure 7:
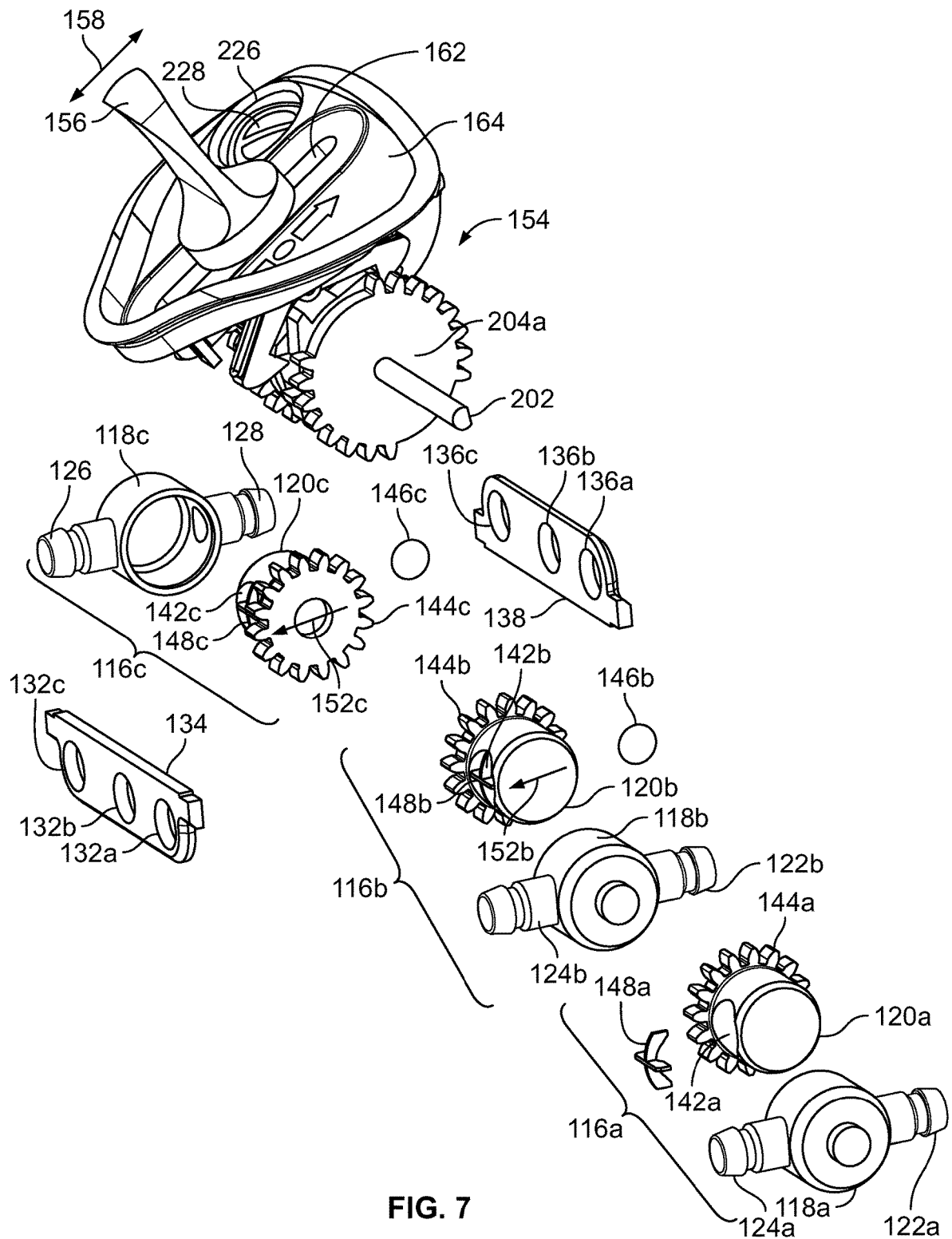
FIG. 7 is an enlarged exploded view of the valve assembly and a perspective view of the toggle mechanism of the controller of FIGS. 1 and 4.

As illustrated in FIGS. 5-7, the controller features a valve assembly that includes three valve mechanisms: flushing valve 116a, balloon valve 116b and reservoir valve 116c. As illustrated in FIGS. 6 and 7, each of valve mechanisms 116a-116c of the valve assembly is preferably a barrel valve that includes a housing 118a, 118b and 118c within which is pivotally mounted a barrel member 120a, 120b and 120c, respectively. Valve housing 118a includes an inlet port 122a and an outlet port 124a. Valve housing 118b similarly includes an inlet port 122b and an outlet port 124b while valve housing 118c includes an inlet port 126 and an outlet port 128. As illustrated in FIGS. 5 and 6, the outlet ports 124a and 124b of valve housings 118a and 118b and the inlet port 126 of valve housing 118c are positioned within the openings 132a, 132b and 132c of a first valve mounting plate 134. The inlet ports 122a and 122b of valve housings 118a and 118b and the outlet port 128 of valve housing 118c are positioned within the openings 136a, 136b and 136c (shown in FIG. 7) of a second valve mounting plate 138. Valve mounting plates 134 and 138 engage the housing halves 74a and 74b so as to secure the valve mechanisms within the controller head portion.

With reference to FIG. 7, each barrel member 120a, 120b and 120c includes a bore 142a, 142b and 142c as well as a gear portion 144a, 144b and 144c. Barrel members 120b and 120c are provided with ball members 146b and 146c positioned within the bores 142b and 142c, respectively. Each of the bores 142b and 142c is provided with an opening on one end that features a chamfered edge and is sized so that the ball members 146b and 146c will not exit. The opposite end of each bore, through which the ball members 146b and 146c are inserted into bores 142b and 142c, and which are visible in FIG. 7, receive grills 148b and 148c in a fixed fashion (such as by adhesive or fasteners). As a result, a ball member is trapped within each bore and causes balloon valve 116b and reservoir valve 116c to act as check valves in that liquid flow may only travel in the direction of arrows 152b and 152c. Barrel member 120a features a similar construction (and thus is provided with grill 148a), but is not provided with a ball member so that it does not act as a check valve.

Internal tubing runs between the outlet port 124a of flushing valve mechanism 116a and the inlet to check valve 114 (FIG. 5). Internal tubing runs between port 112b and the outlet port 124b of balloon valve mechanism 116b. Internal tubing also runs between port 112c and inlet port 126 of reservoir valve mechanism 116c. The internal tubing described above is not shown for ease of illustration.

The inlet port 122a of flushing valve mechanism 116a is received within bellows port 86a (of FIG. 5). The inlet port 122b of balloon valve mechanism 116b is received within bellows port 86b. The outlet port 128 of reservoir valve mechanism 116c is received within bellows port 86c.

Figure 8:
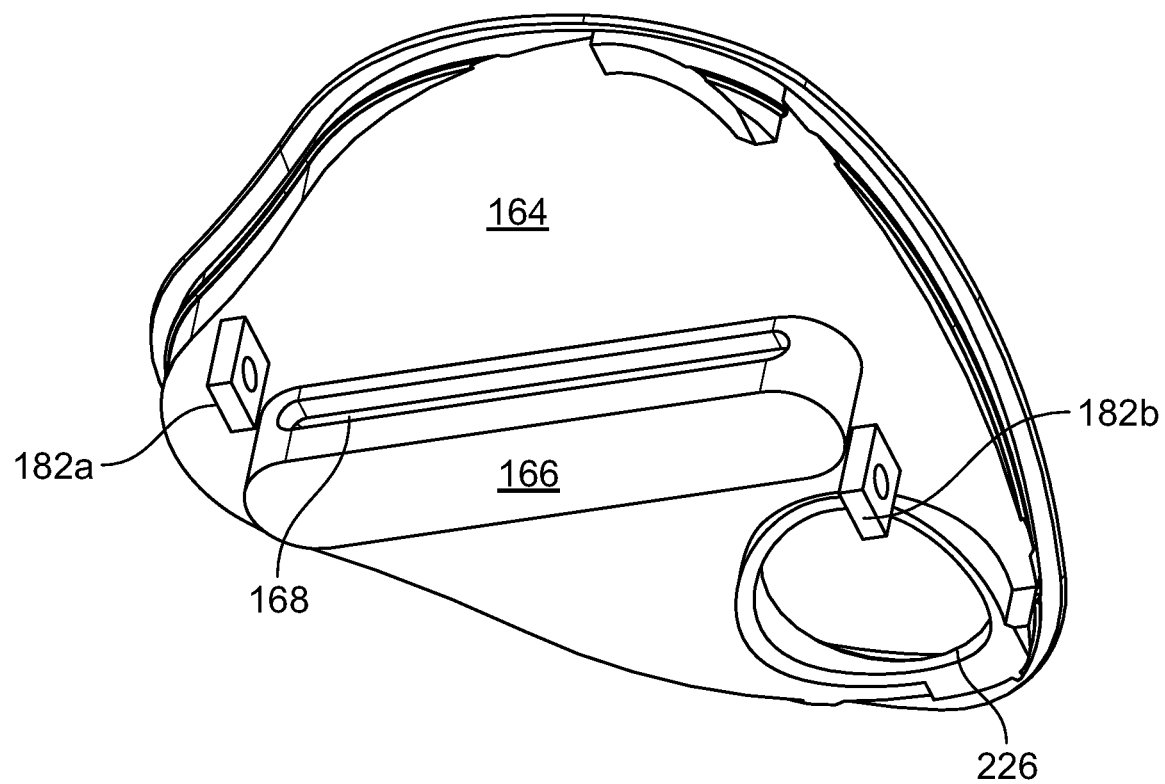
FIG. 8 is an enlarged bottom perspective view of the control panel of the toggle mechanism of FIG. 7.
Figure 9:
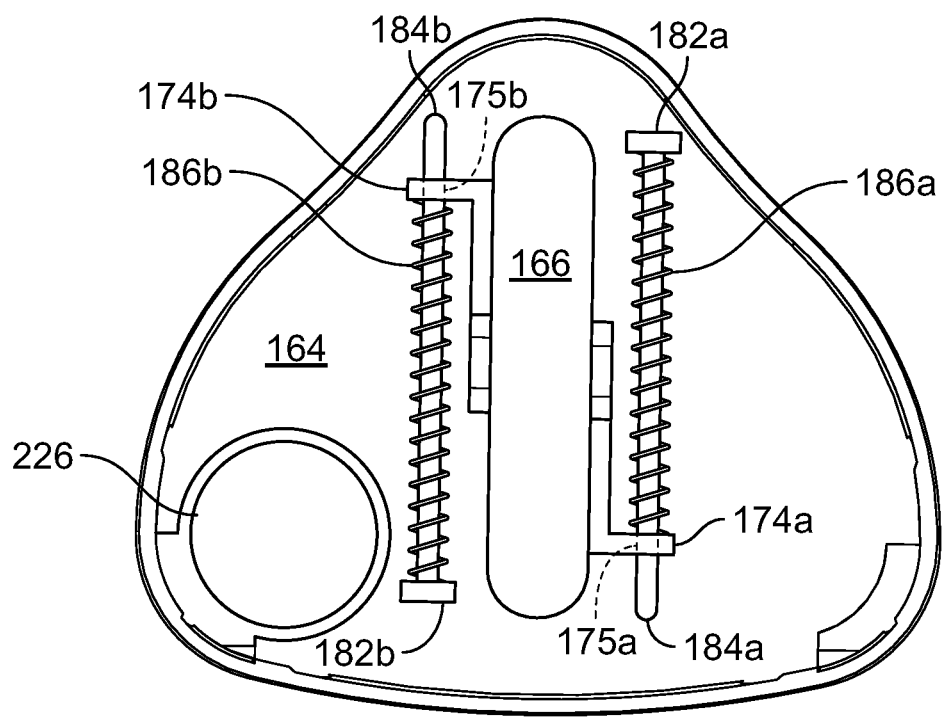
FIG. 9 is a bottom plan view of the control panel of FIG. 8 with the toggle switch assembly added.
Figure 10:
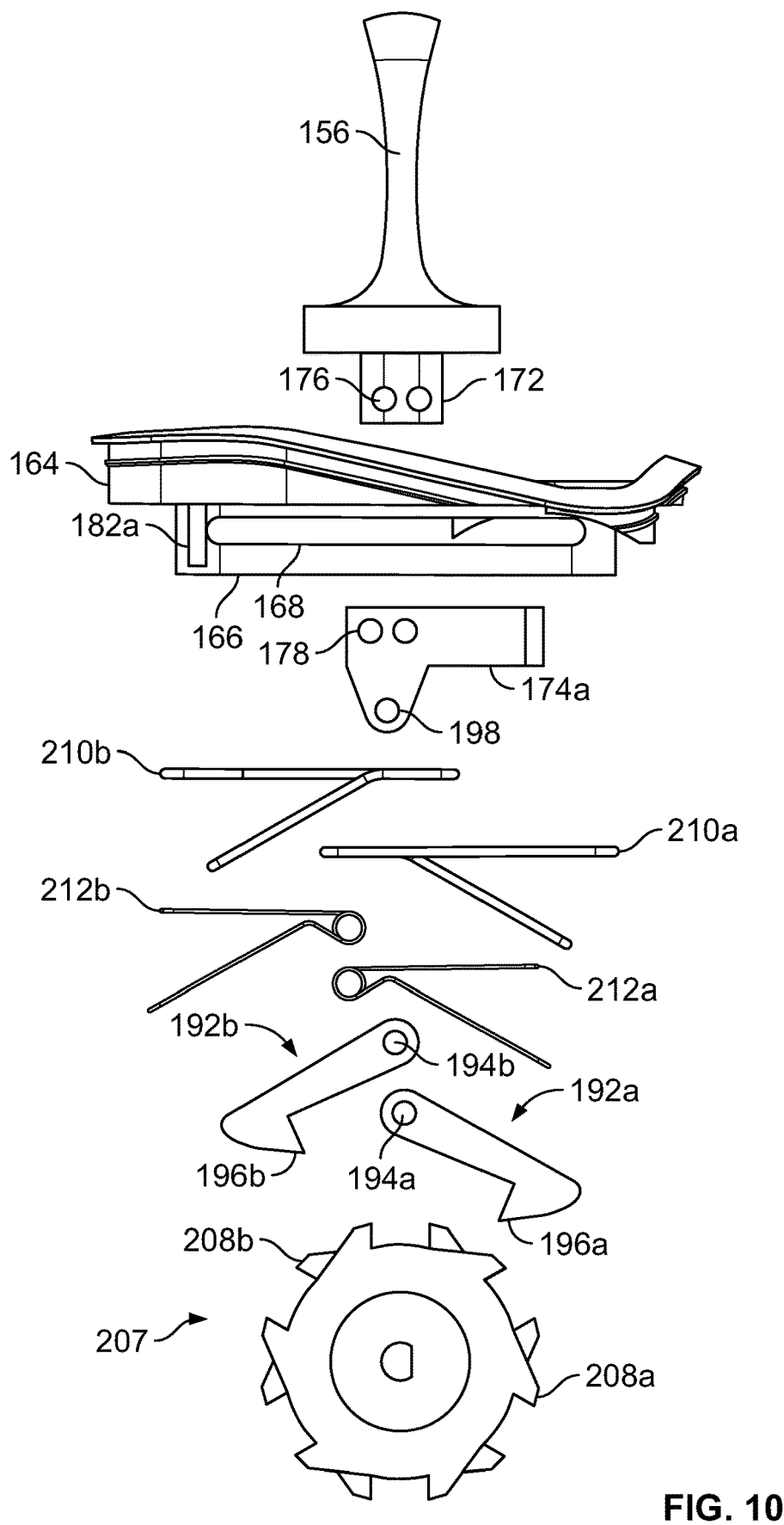
FIG. 10 is an exploded side elevational view of the toggle mechanism of FIG. 7.

The controller features a toggle mechanism, indicated in general at 154 of FIG. 7, that includes a toggle switch 156 that may be moved from the rest position shown in FIG. 7 in the direction of arrows 158 to reconfigure the valves as described below. The toggle switch slides within an elongated trough 162 formed in a control panel 164. The bottom side of the trough is indicated at 166 in FIGS. 8-10. As illustrated in FIGS. 8 and 10, the trough also features sidewalls having elongated openings 168. As shown in FIG. 10, a mounting stem 172 is secured to the bottom of the toggle switch 156 and is received within the elongated trough 162. A pair of sliding L-shaped spring retainers, illustrated at 174a and 174b of FIGS. 9 and 10, are secured to the stem 172 on opposite sides of the trough. More specifically, pins pass through the pair of openings 176 of stem 172, elongated openings 168 in the trough sidewalls, pair of openings 178 of spring retainer 174a and corresponding openings of spring retainer 174b.

As shown in FIGS. 8 and 9, the bottom side of the control panel features tabs 182a and 182b to which are secured spring guide rods 184a and 184b, respectively, in a fixed fashion. Spring retainers 174a and 174b each feature an opening (illustrated in phantom in FIG. 9 at 175a and 175b) that receives a corresponding one of the spring guide rods 184a and 184b, respectively. These spring retainer openings 175a and 175b are sized so that the spring retainers slide along the spring guide rods as the toggle switch is manipulated in the direction of arrows 158 (FIG. 7). Compression coil springs 186a and 186b (FIG. 9) are concentrically positioned on spring guide rods 184a and 184b and are engaged on opposite ends by the tabs 182a and 182b and the spring retainers 174a and 174b. As a result, toggle switch 156 is urged towards the central rest position illustrated in FIG. 7 and the compression coil springs 186a and 186b of FIG. 9 are alternatively compressed as the toggle switch is moved in either direction of arrows 158 (FIG. 7).

Figure 11:
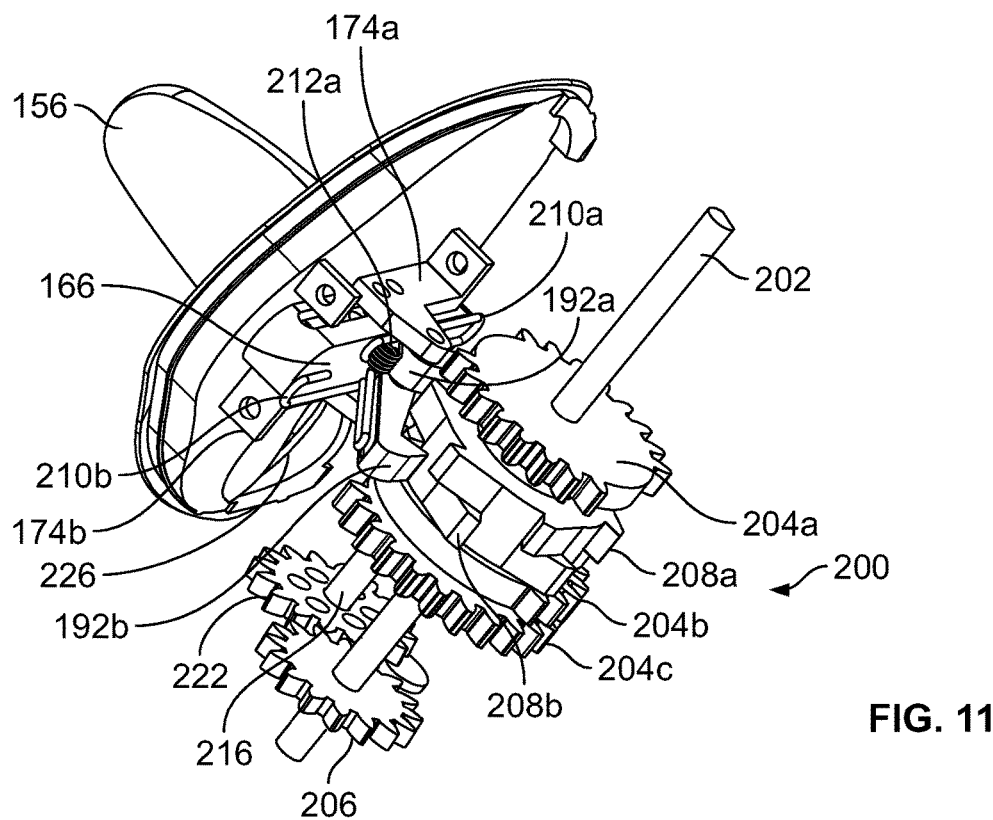
FIG. 11 is an enlarged rear perspective view of the toggle mechanism of FIGS. 7 and 10.

With reference to FIG. 10, a pair of pawls 192a and 192b having proximal ends featuring openings 194a and 194b and distal ends having hook portions 196a and 196b. As illustrated in FIG. 11, the proximal ends of pawls 192a and 192b are pivotally mounted to and between spring retainers 174a and 174b. More specifically, with reference to FIG. 10, a pin passes through the openings 194a and 194b of the pawls 192a and 192b and corresponding openings of spring retainers 174a and 174b (shown at 198 in FIG. 10 for spring retainer 174a).

Figure 12:
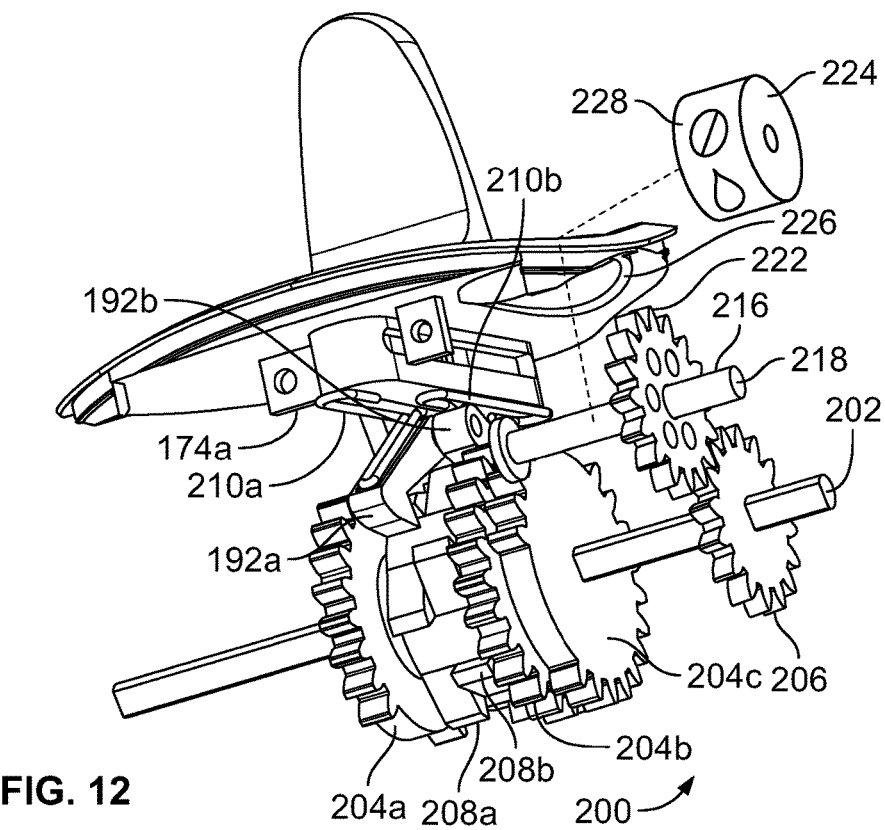
FIG. 12 is a front perspective view of the toggle mechanism of FIG. 11.

Spring retainer 174b is absent from FIGS. 10 and 12 for ease of illustration.

A valve gear train, indicated in general at 200 in FIGS. 11 and 12, features a D-shaped shaft 202 upon which is mounted valve configuration gears 204a, 204b and 204c. In addition an indicator wheel lower gear 206 is mounted on the shaft. The ends of shaft 202 are pivotally mounted within the head portion of the housing of the controller.

A ratchet wheel (indicated in general at 207 in FIG. 10) is also mounted on the shaft 202 between valve configuration gears 204b and 204c and includes a first set of ratchet teeth 208a and a second set of ratchet teeth 208b. With reference to FIGS. 10-12, a first pair of springs 210a and 212a engage the bottom 166 of the control panel trough and the top surface of the pawl 192a and cooperate to urge the hook portion 196a into engagement with the teeth 208a of the ratchet wheel. A second pair of springs 210b and 212b similarly cooperates to urge the hook portion 196b of pawl 192b into engagement with the teeth 208b of the ratchet wheel. Spring 212b is missing from FIG. 12 for ease of illustration.

In operation, as the toggle switch 156 is moved in the direction of arrows 158 of FIG. 7, the pawl hook portions 196a and 196b (FIG. 10) alternatively engage the teeth 208a and 208b of the ratchet wheel, respectively, so that the shaft 202 (FIGS. 11 and 12) of the valve train, and thus the valve gears of the valve train, are rotated either clockwise or counterclockwise (depending on the direction of movement of the toggle switch).

The gear portions 144a, 144b and 144c (FIG. 7) of the valve mechanisms 116a, 116b and 116c are engaged and turned by the valve gears 204a, 204b and 204c (FIGS. 11 and 12), respectively. As a result, the configurations of the valve mechanisms are controlled by the movement of the toggle switch 156, as will be described in greater detail below.

As shown in FIGS. 11 and 12, an indicator wheel shaft 216 is pivotally mounted by end 218 within the head portion of the controller housing. An upper indicator wheel gear 222 is secured to the shaft 216 in a fixed fashion, as is an indicator wheel 224 (not shown in FIG. 11 for ease of illustration). Upper indicator wheel gear 222 is engaged by lower indicator wheel gear 206 and thus is turned, as is shaft 216 and indicator wheel 224, when the gear train shaft 202 is turned. The indicator wheel is positioned below an indicator window 226 formed in control panel 164. The indicator wheel includes setting icons 228 that appear in the indicator window based on the setting of the valve mechanism as directed by the manipulation of the toggle switch 156.

As illustrated in FIG. 1, the system tubing 52, 54a and 54b and drain valve control line sheath 56 are preferably connected to the controller by a tubing and drain valve line connector 232. The tubing and drain valve control line connector is indicated in general at 232 in FIGS. 13-15B. As noted previously, the bottom of the handle portion of the controller is provided with controller connector ports 112a, 112b and 112c. The connector 232 features four main components: a cover 234, a main housing 236, a drain valve line sliding connector 238 and a handle housing 242.

The housing 236 of the tubing and drain valve line connector 232 features a pair of cylindrical portions 243a and 243b that include bores 244a and 244b. The open top ends of bores 244a and 244b receive the controller connector ports 112a and 112b in a liquid sealing but removable fashion. The open bottom ends of bores 244a and 244b are connected to the ends of tubing 54a and 54b (FIG. 1). Handle housing 242 includes a handle portion 243, that may be easily engaged by a user's finger, and a bore 244c having an open top end which receives controller connector port 112c in a liquid sealing but removable fashion. The open bottom end of bore 244c is connected to the end of tubing 52.

A passageway 246 (FIG. 14) is defined between the cylindrical portions 243a and 243b of the housing and the handle housing 242. The drain valve line sliding connector 238 is positioned within the passage, as shown in FIGS. 13, 15A and 15B, and is movable between the positions illustrated in FIG. 15A (FIG. 13) and 15B.

Figure 14:
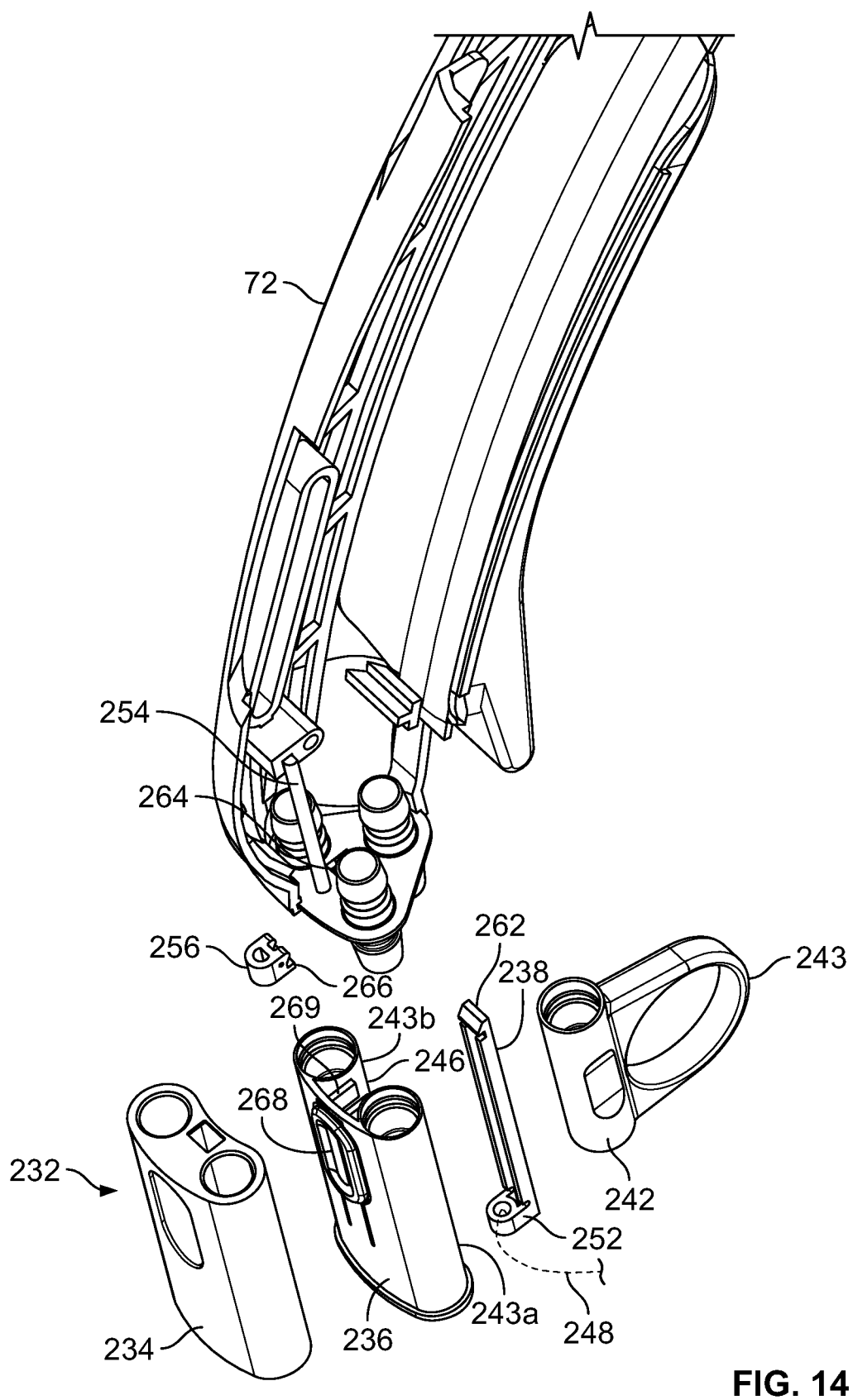
FIG. 14 is an exploded view of the tubing and drain valve line connector of FIG. 13.
Figure 15B:
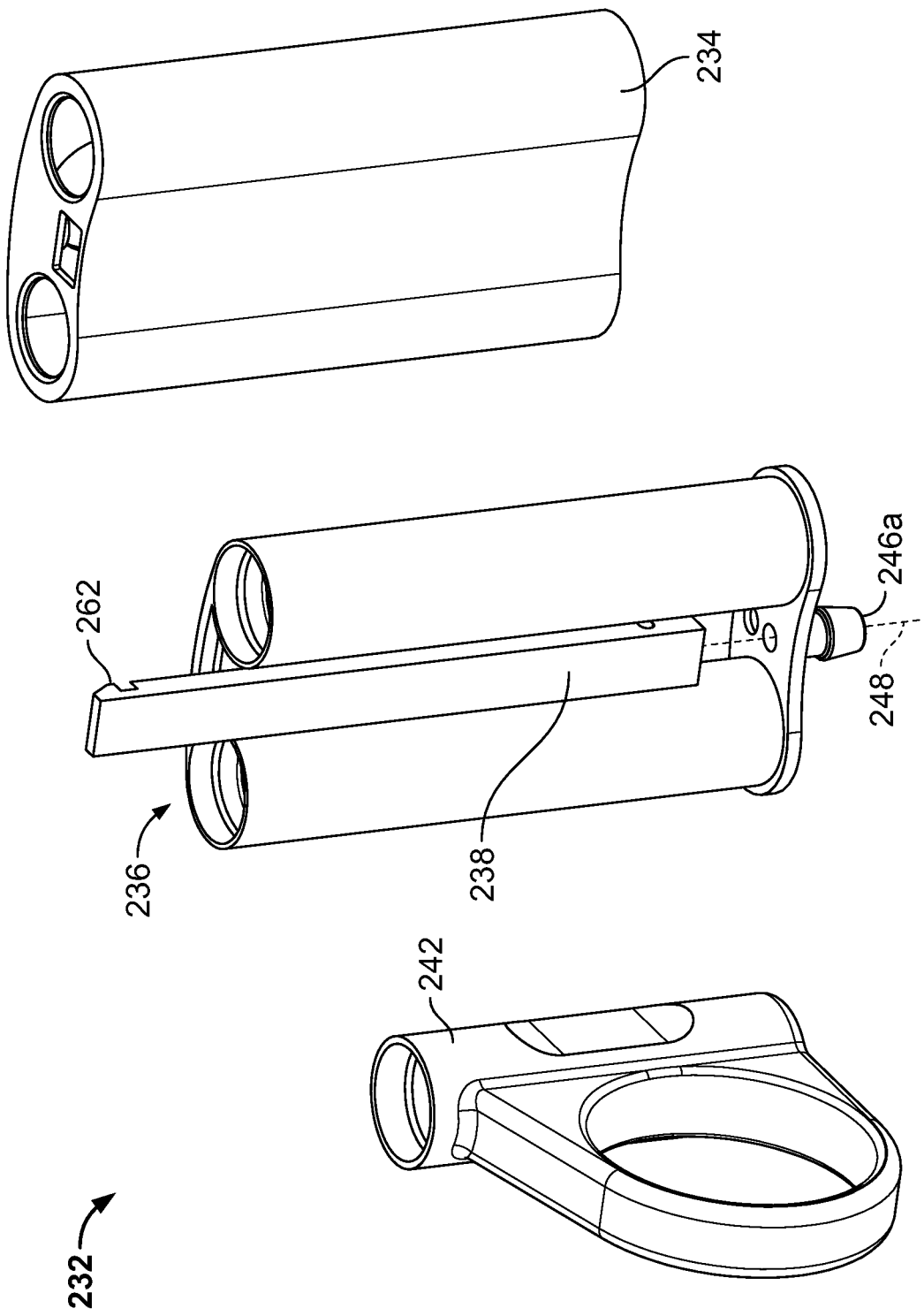

The end of waste drain valve control line sheath 56 (FIG. 1) nearest the controller is connected to fitting 246a of FIGS. 15A and 15B. A waste drain valve control line or cord, illustrated in phantom at 248 in FIGS. 14 and 15B is housed within the sheath 56 and, as illustrated in FIG. 14, has a proximal end that is attached to the opening of a tab 252 formed on the bottom end of the sliding member 238.

Figure 13:
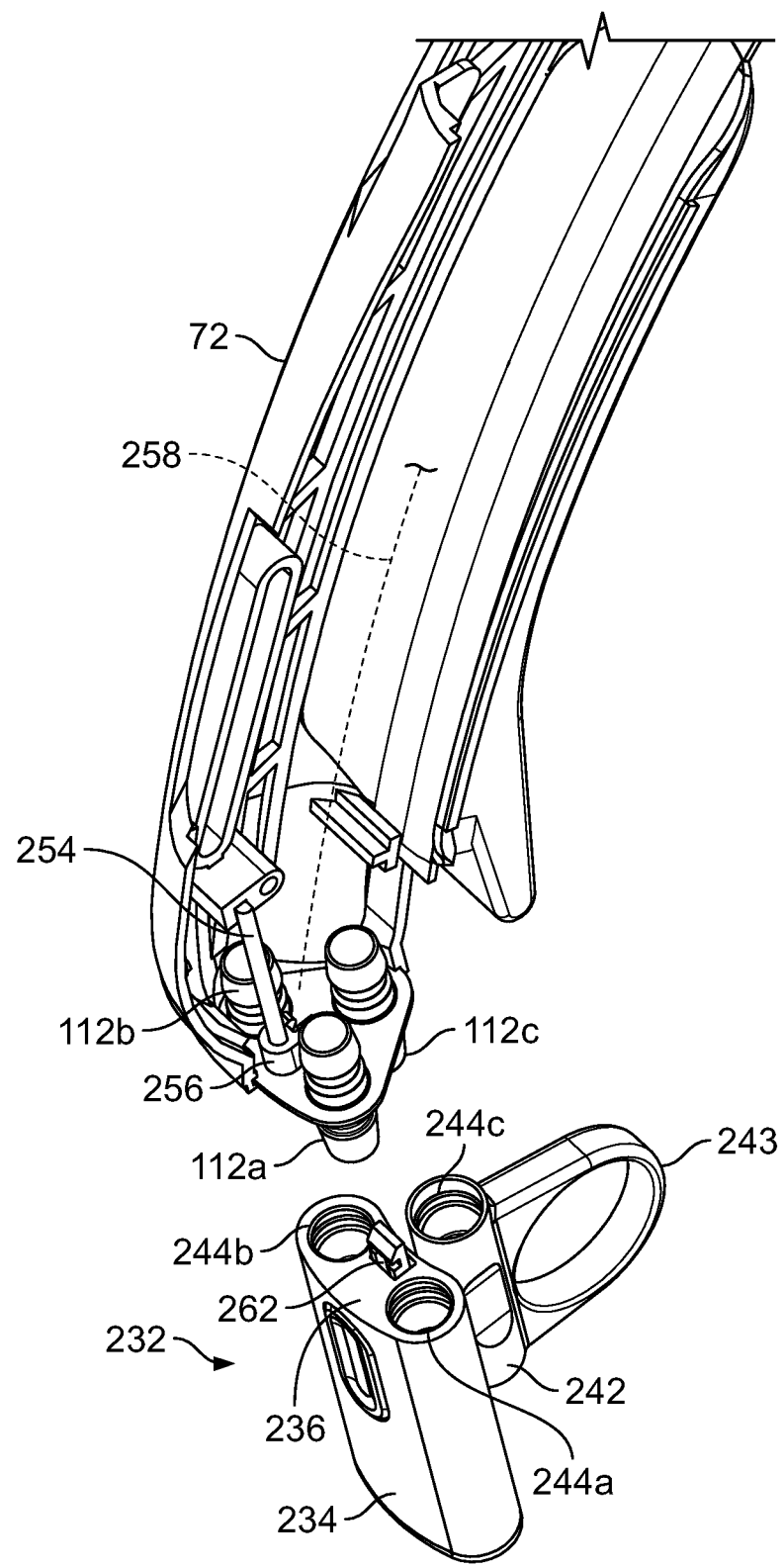
FIG. 13 is an enlarged perspective view of the bottom of the handle portion of the controller of FIG. 4 and a perspective view of a tubing and drain valve line connector prior to attachment to the controller.

As shown in FIGS. 13 and 14, a D-shaped latching member guide rod 254 is mounted in the bottom of the handle portion of the controller. A latching member 256 features a D-shaped opening that receives the guide rod 254 so that the latching member is free to traverse the rod. The bottom end of an internal drain valve control line, illustrated in phantom at 258 in FIG. 13, is attached to the latching member 256.

When the tubing and drain valve control line connector 232 is connected to the controller, in the manner illustrated in FIG. 1, a hook portion 262 (FIGS. 13-15B) of the sliding connector 238 passes through an opening (264 of FIG. 14) through the bottom of the handle portion of the controller and engages a corresponding ledge 266 (FIG. 14) formed on the latching member 256. As a result, when the internal drain valve control line 258 of FIG. 13 is pulled upwards, latching member 256 slides up along guide rod 254 and pulls sliding connector 238 upwards with it, as illustrated in FIGS. 15A and 15B. This causes the drain valve control line 248 of FIG. 15B to also be pulled upwards and into the housing 236 of the tubing and drain valve control line connector, as illustrated in FIG. 15B. As will be explained in greater detail below, the distal end of line 248 is connected to a drain valve actuator mechanism in the catheter hub (48 of FIG. 1) so as to open a waste drain valve of catheter 46.

As shown in FIG. 14, the connector housing 236 is provided with a push button 268 having a pair of tabs 269 on its back side. The tabs 269 move the hook portion 262 of the sliding connector 238 in a direction away from the latching member 256 when the push button 268 is pressed so that the tubing and drain valve control line connector 232 is free to be removed from the controller.

The top end of the internal drain valve control line 258 of FIG. 13 is connected to a drain valve switch sliding carriage, indicated in general 272 in FIG. 6. The carriage includes a base 274 with notches 276 that receive and travel along tracks 278 formed on the interior surfaces of the controller housing halves.

As illustrated in FIGS. 1 and 6, an elongated slot 282b is formed in controller housing half 74b so that the shaft of a sliding switch 284b may be connected via a mounting hole 286b to the side portion 288b of drain valve switch sliding carriage 272. Sliding switch 284a is connected to carriage side portion 288a via mounting hole 286a in a similar fashion.

The drain valve switch sliding carriage 272 is urged in the direction of arrow 292 of FIG. 6 by a spring linkage indicated in an exploded condition in general at 294. The assembly includes a bottom link 296 which is pivotally mounted to opening 298a of the carriage side portion 288a and features a upwardly extending dowel 302. A top link 304 is pivotally mounted to the interior surface of controller housing half 74a (FIG. 4) and features a downward facing cylinder 306 that receives dowel 302 in a telescoping fashion. A compression coil spring 308 is concentrically mounted over cylinder 306 and dowels so as to urge the top and bottom links away from one another. A similar spring linkage is connected between the interior surface of housing half 74b and the opening 298b of carriage 272.

As described above with respect to FIG. 1, the controller 40 is used to provide a lavage liquid, such as water, to a catheter 46 for performing transanal irrigation. The catheter is held by hub 48. The hub 48 is connected to system tubing 54a, 54b and sheath 56 that leads to and from controller 42. As illustrated in FIGS. 17A and 17B, the catheter 46, which is preferably disposable, is removably held by the hub 48, which is preferably non-disposable. As illustrated in FIGS. 17B-18B, the catheter 46 includes a base, indicated in general at 312, that houses a catheter drain or waste valve 313. The drain or waste valve 313 includes a barrel valve member 314 having a drain passage 316 (FIGS. 18A and 18B) there through. The barrel valve member 314 also includes a parallel pair of recesses 318a and 318b on each side.

Figure 21:
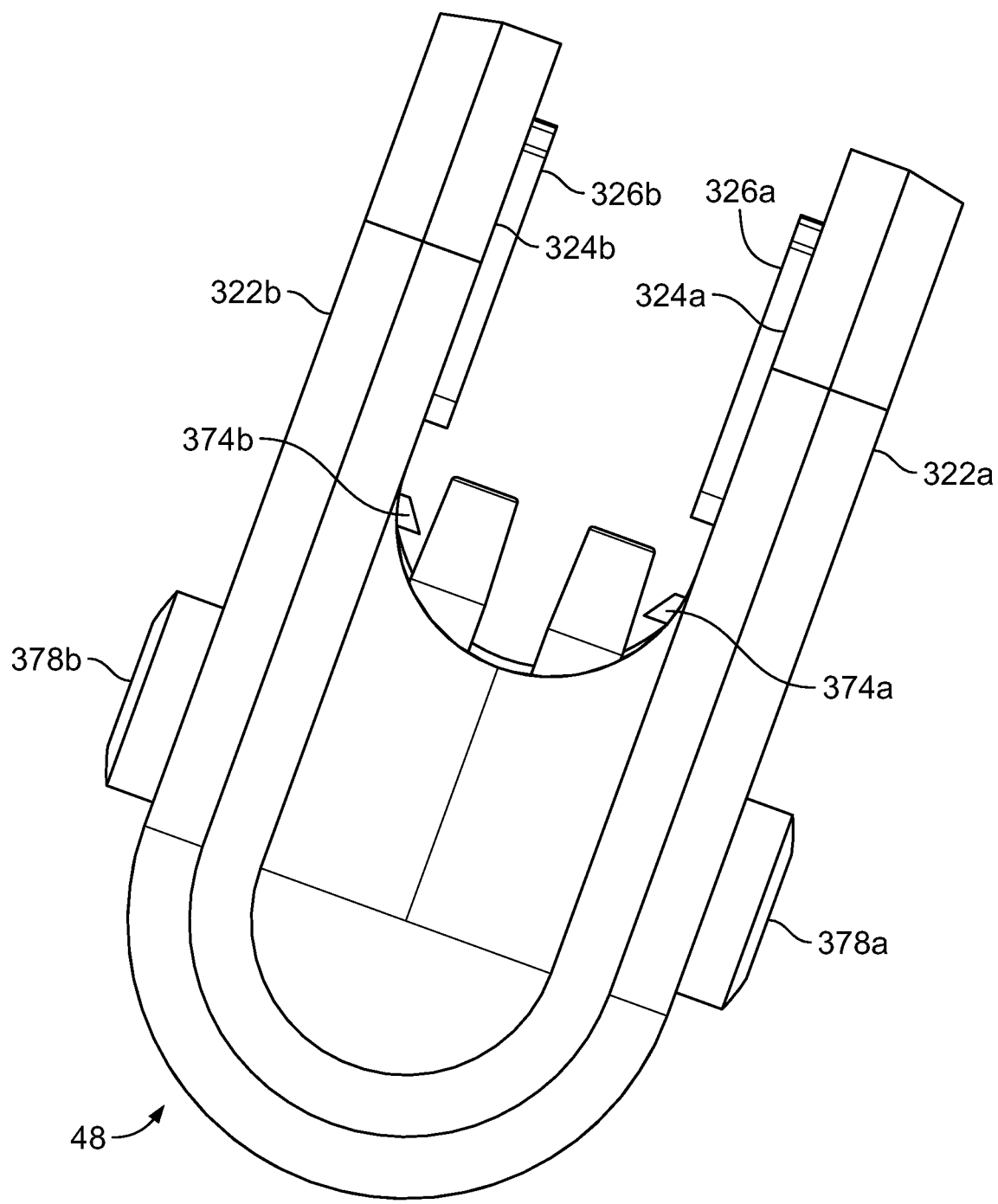
FIG. 21 is an enlarged top plan view of the hub of FIGS. 17B-18B.

The hub 48 includes a pair of spaced wings 322a and 322b that define a generally U-shaped cavity that removably receives the base 312 of the catheter 46. As illustrated in FIGS. 17B-18B and 21, the inner surface of wing 322a is provided with a pivoting disk 324a that includes a pair of parallel ridges 326a. The inner surface of wing 322b features a pivoting disk 324b (FIG. 21) that is the mirror image of pivoting disk 324a and that includes a pair of parallel ridges 326b (FIG. 21). When the base 312 of the catheter 46 is positioned within the generally U-shaped cavity of hub 48, in the manner illustrated in FIG. 17A, the ridges 326a of pivoting disk 324a of the hub engage the recesses 318a of the barrel valve member 314 of the catheter, and the ridges 326b of the corresponding pivoting disk of the hub engage the recesses 318b of the barrel valve member 314 of the catheter.

Figure 19A:
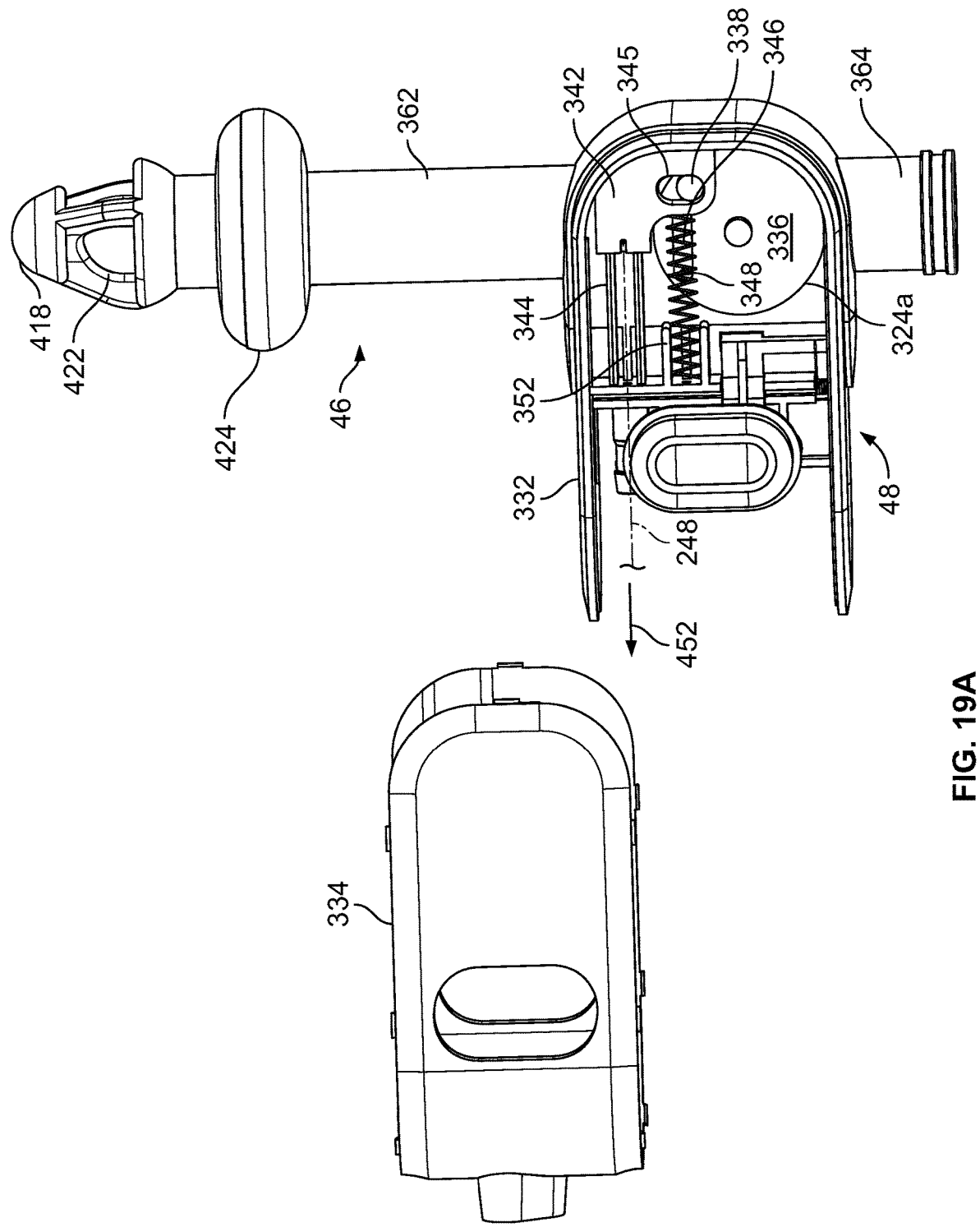
FIGS. 19A and 19B are exploded perspective views of the catheter and hub of FIGS. 17A and 18B with the hub housing cover removed with the catheter drain valve in the closed and open configurations, respectively.

Turning to FIG. 19A, the hub, indicated in general at 48, includes a hub housing 332 and a hub housing cover 334. The pivoting disk 324a includes a backside or an inner surface 336 that is positioned within the hub housing and is provided with a pin 338. Pin 338 is fixed to the surface 336. A motion converter 342 is positioned is positioned within the hub housing 332 and slides along tracks 344. The motion converter 342 features a slot 345 which receives pin 338 of the pivoting disk. The motion converter also includes a spring mounting pin 346. A compression coil spring 348 concentrically receives the spring mounting pin 346 through one end, while the opposite end of the spring is received within a recess 352 formed within the hub housing.

Figure 19B:
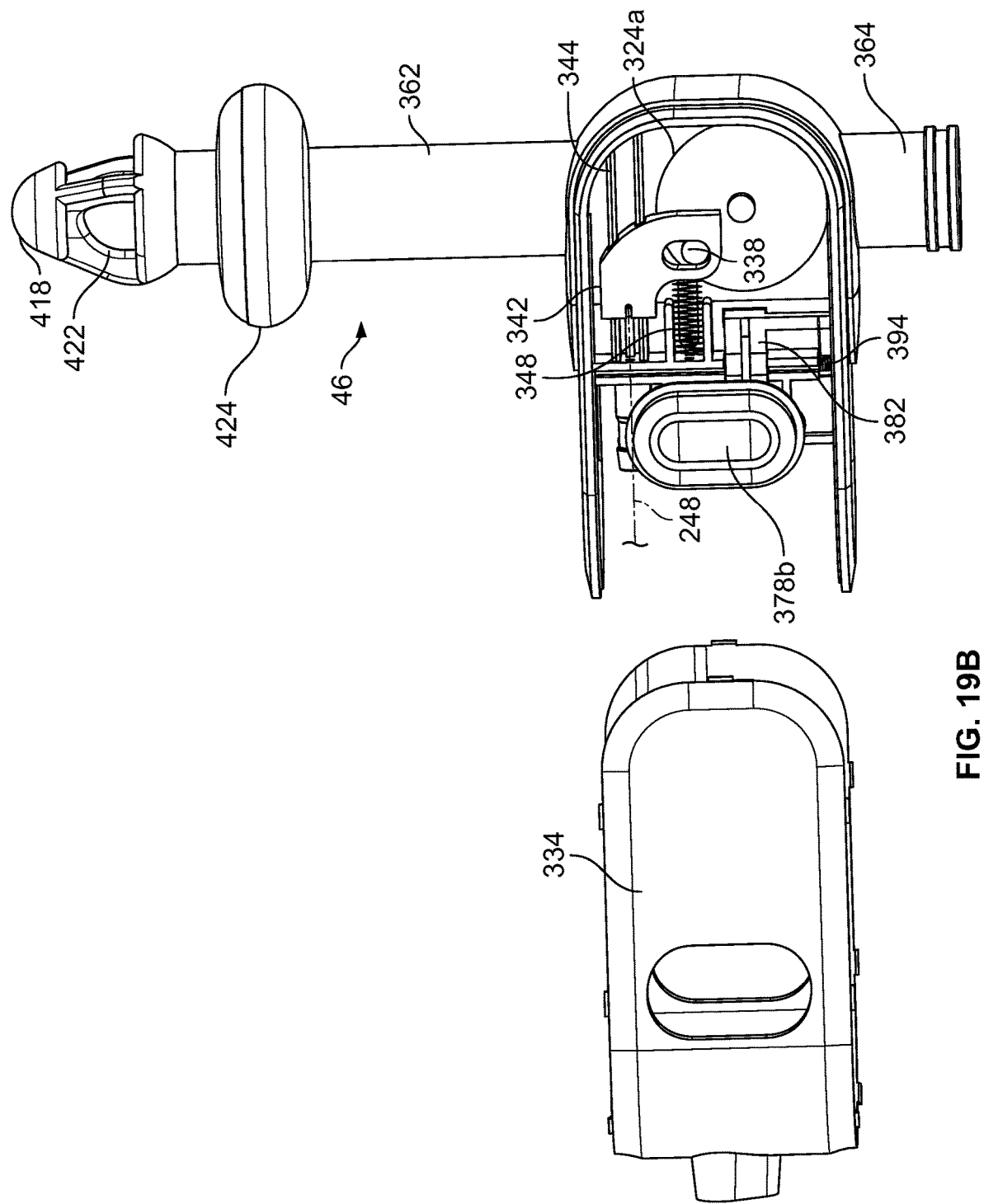

The pivoting disk 324b (FIG. 21) of wing 322b is provided with a mechanism that is similar to the one illustrated and described for pivoting disk 324a of FIGS. 19A and 19B.

Figure 18A:
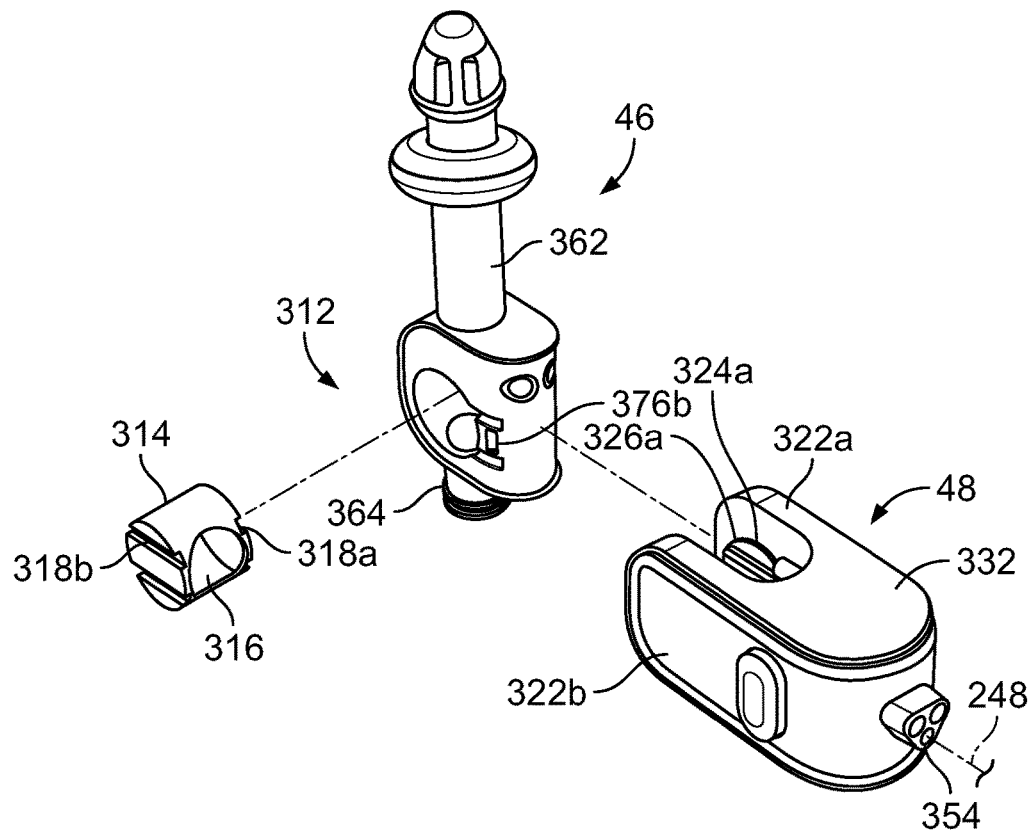
FIGS. 18A and 18B are exploded perspective views of the drain valve barrel member of the catheter of FIGS. 17A and 17B with the barrel member in the closed and open positions, respectively.
Figure 18B:
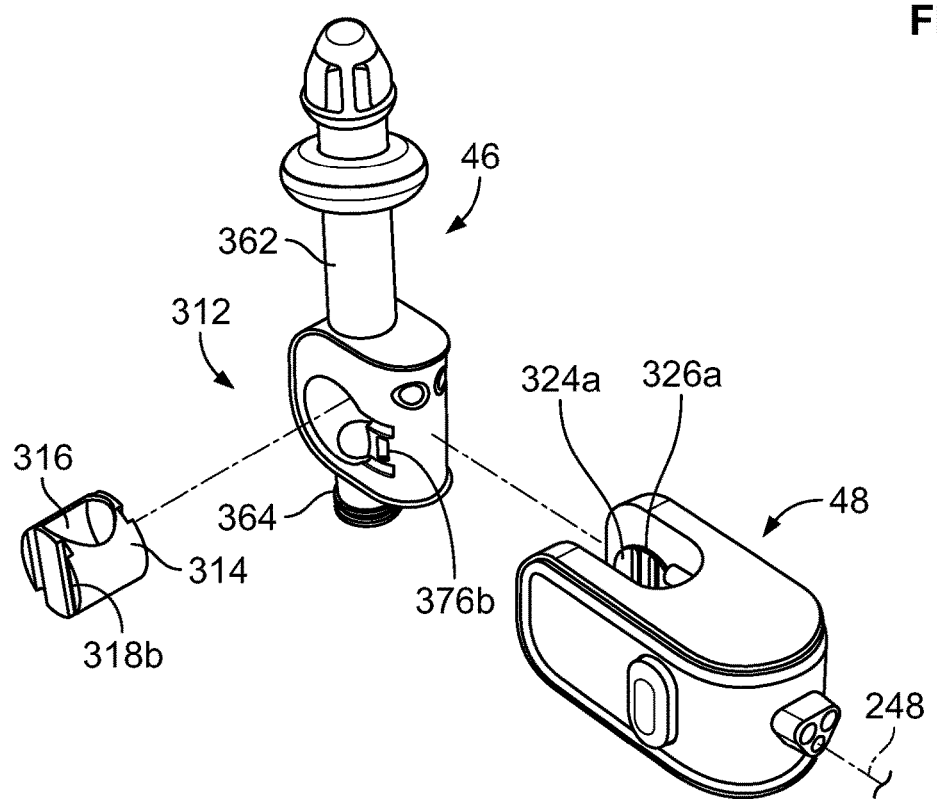

As illustrated in FIGS. 19A and 19B, the drain valve control line 248 (introduced previously with reference to FIGS. 14 and 15B), is secured by an end to the motion converter 342 and, as illustrated in FIGS. 18A and 18B, exits the hub housing 332 through the port 354 (to which sheath 56 of FIG. 1 is attached). Line 248 splits after entering the hub housing 332 so that it also is connected to the motion converter attached to pivoting disk 324b (FIG. 21). As a result, the position of the motion converter attached to pivoting disk 324b mirrors the position of motion converter 342.

As described previously with respect to FIGS. 14 and 15B, the waste drain valve control line 248 has a proximal end attached to a drain valve line sliding connector 238, which connects to a latching member 256. As illustrated in FIG. 13, an internal waste drain valve control line 258 is attached to a sliding latching member 256 within the controller which, when the system is in use, is connected to the waste drain valve line sliding connector 238.

When the pivoting disk 324a is positioned as illustrated in FIG. 19A, the ridges 326a of the pivoting disk are oriented as illustrated in FIGS. 17B, 18A and 21. When the pivoting disk 324a is positioned as illustrated in FIG. 19B, the ridges 326a of the pivoting disk are as illustrated in FIG. 18B. The orientation of ridges 326b of pivoting disk 324b (FIG. 21) mirror the orientation of ridges 326a of pivoting disk 324a.

Figure 26:
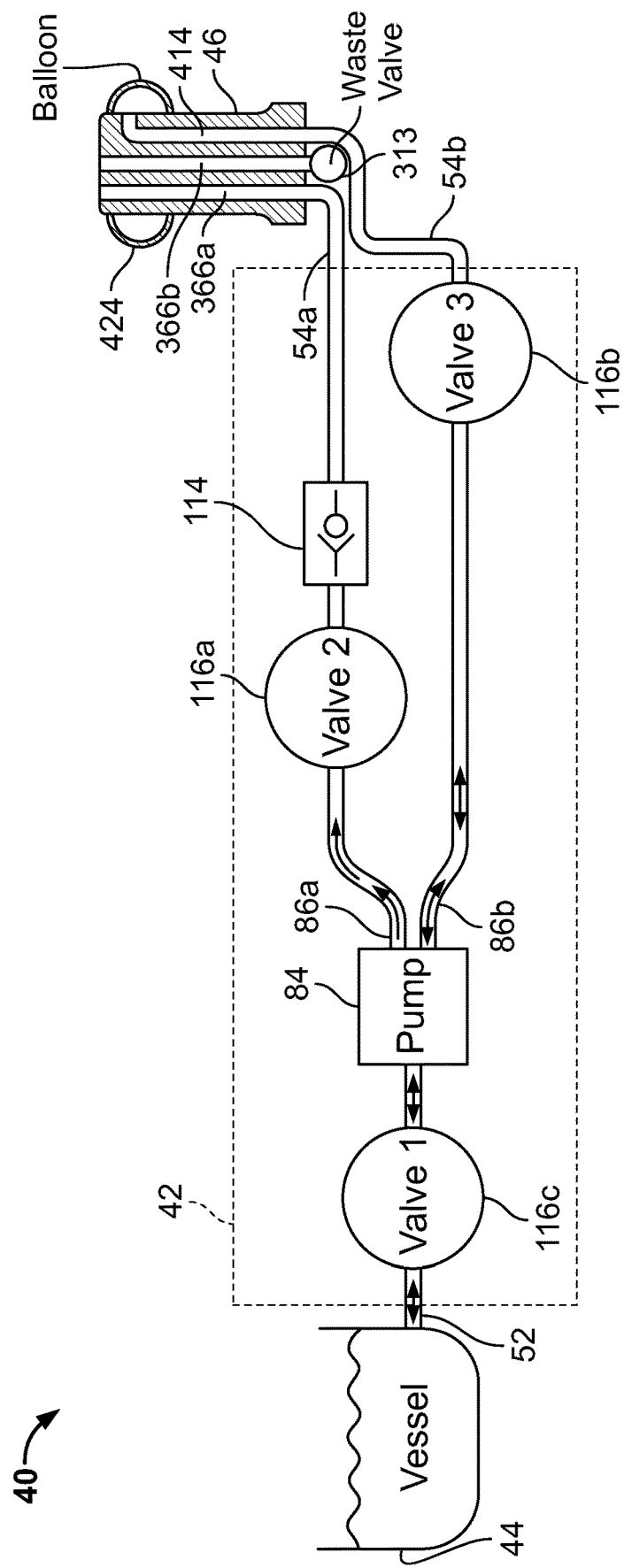
FIG. 26 is a schematic view of the system of FIG. 1.

As illustrated in in FIGS. 18A-19B, the catheter 46 includes an upper stem 362 and a lower stem 364. As noted previously, the catheter also includes a base, indicated in general at 312 in FIGS. 17B-18B, that houses a waste drain valve including barrel valve member 314 with a drain passage 316 there through. These components are shown schematically in FIGS. 20A and 20B, where a combination flushing and upper drain passage 366 in the catheter upper stem 362 and a lower drain passage 368 in the catheter lower stem 364 are illustrated. The flushing passage could alternatively be formed separately from the drain passage (as illustrated in FIG. 26) or the flushing passage may take the form of tubing positioned within the upper drain passage 366.

Figure 20A:
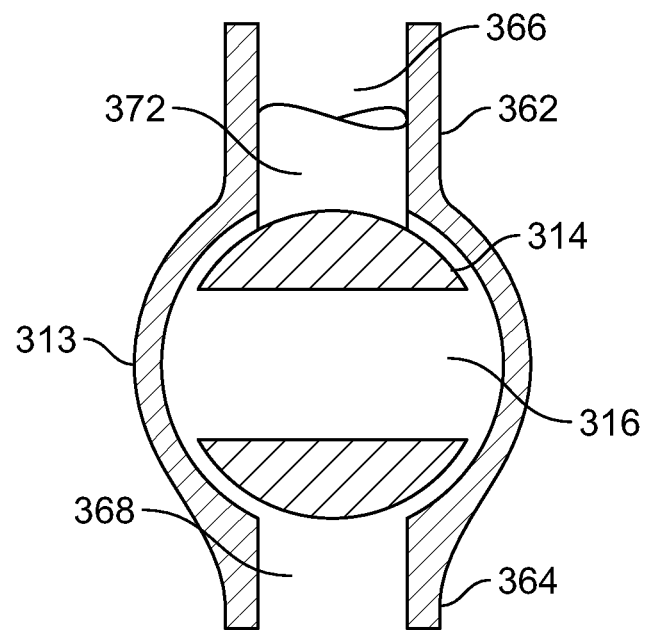
FIGS. 20A and 20B are schematic views of the drain valve of the catheter of FIGS. 17A-19B in the closed and open configurations, respectively.
Figure 20B:
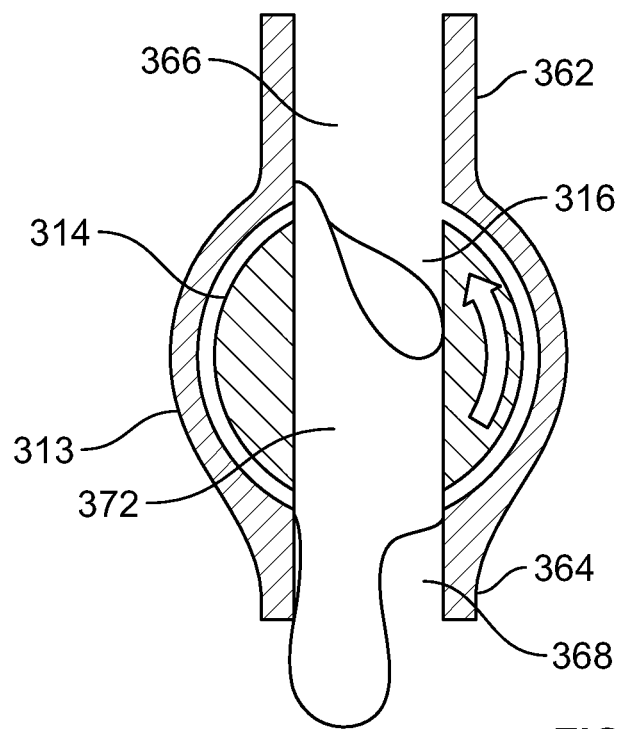

When the barrel valve member 314 is positioned with its barrel valve passage 316 oriented as in FIG. 20A (and FIG. 18A), the catheter waste drain valve is in the closed configuration and liquid 372, which includes irrigation liquid, liquefied feces and other waste, is retained in upper drain passage 366 of the catheter and in the body cavity of the user. When the barrel valve member 314 is positioned with its barrel valve passage 316 oriented as in FIG. 20B (and FIG. 18B), that is, with passage 316 in alignment with upper drain passage 366 and lower drain passage 368, the catheter drain valve is in the open configuration and the liquid and waste 372 flows through the catheter and exits through an opening in the bottom of the lower stem 364 into a toilet or other disposal destination.

As noted previously, when configured for use in performing TAI, the catheter 46 is positioned within the generally U-shaped cavity of hub 48, in the manner illustrated in FIG. 17A. As shown in FIG. 21, the interior of the U-shaped cavity of hub 48 is provided with a pair of retractable locking hooks 374a and 374b. When the catheter is installed within the hub, as illustrated in FIGS. 17A, 19A and 19B, locking hook 374b engages a corresponding locking notch 376b (FIGS. 17B-18B) formed in the base 312 of the catheter. Locking hook 374a engages a similar locking notch (not shown) formed in the catheter base. As a result, the catheter 46 is locked in the hub 48.

Figure 22:
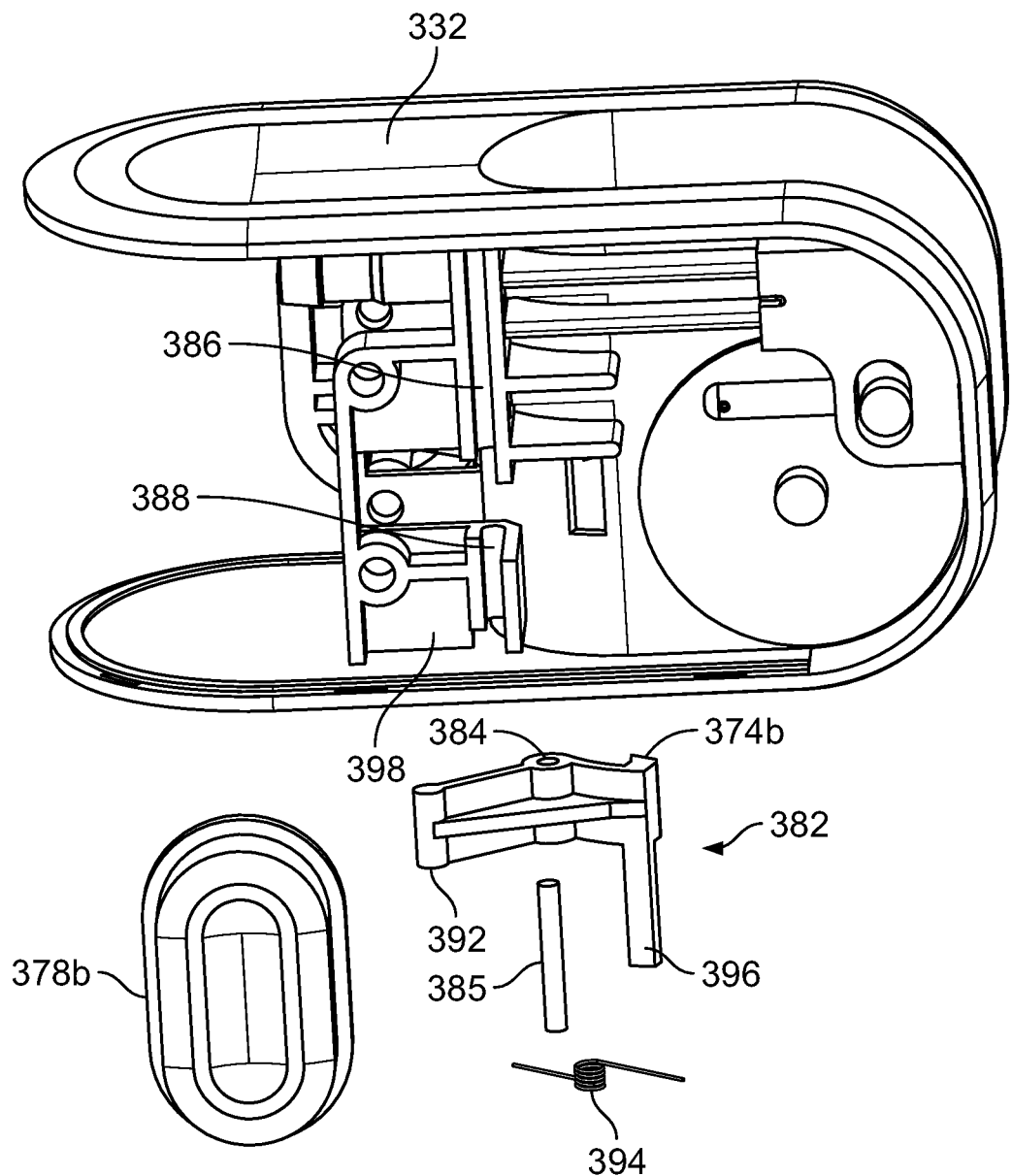
FIG. 22 is an exploded view of the base latching mechanism of the hub of FIGS. 17B-18B.

A pair of release buttons 378a and 378b (FIG. 21) are functionally connected to the locking hooks 374a and 374b of the hub 48. More specifically, with reference to FIG. 22, a pivoting member, indicated in general at 382, includes the locking hook 374b and is pivotally mounted within the hub housing by a central portion opening 384 that receives a pin 385. The pin is received within recesses 386 and 388 formed within the hub housing. Release button 378b is mounted to a button mount 392 of the pivoting member. A torsion spring 394 receives the bottom end of pin 385 and engages pivot member leg 396 and wall 398 within the hub housing (as shown in FIG. 19B). As a result, the release button 378b and locking hook 374b are urged into the positions shown in FIG. 21. When the release button 378b is pressed, however, the locking hook 374b disengages the locking notch 376b (FIGS. 17B-18B) of the catheter base and is retracted into the hub housing. Release button 378a and locking hook 374a are joined by a similar mechanism. Therefore, when the release buttons 378a and 378b are pressed, the locking members 374a and 374b retract, and the catheter 46 may be removed from the hub 48.

Figure 23:
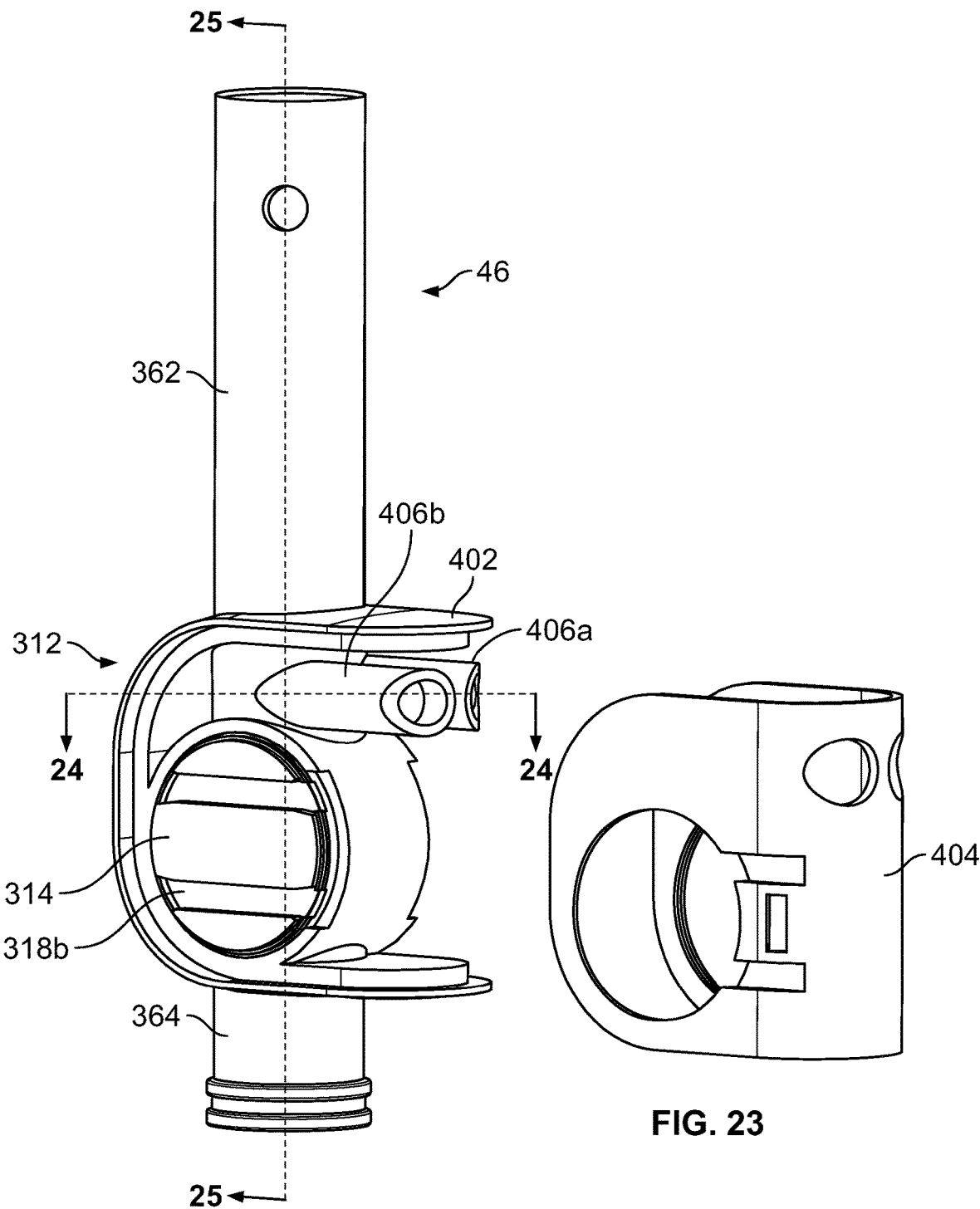
FIG. 23 is a perspective view of the housing of the catheter of FIGS. 17B-18B with the housing cover removed and the waste drain valve in the closed configuration.
Figure 24:
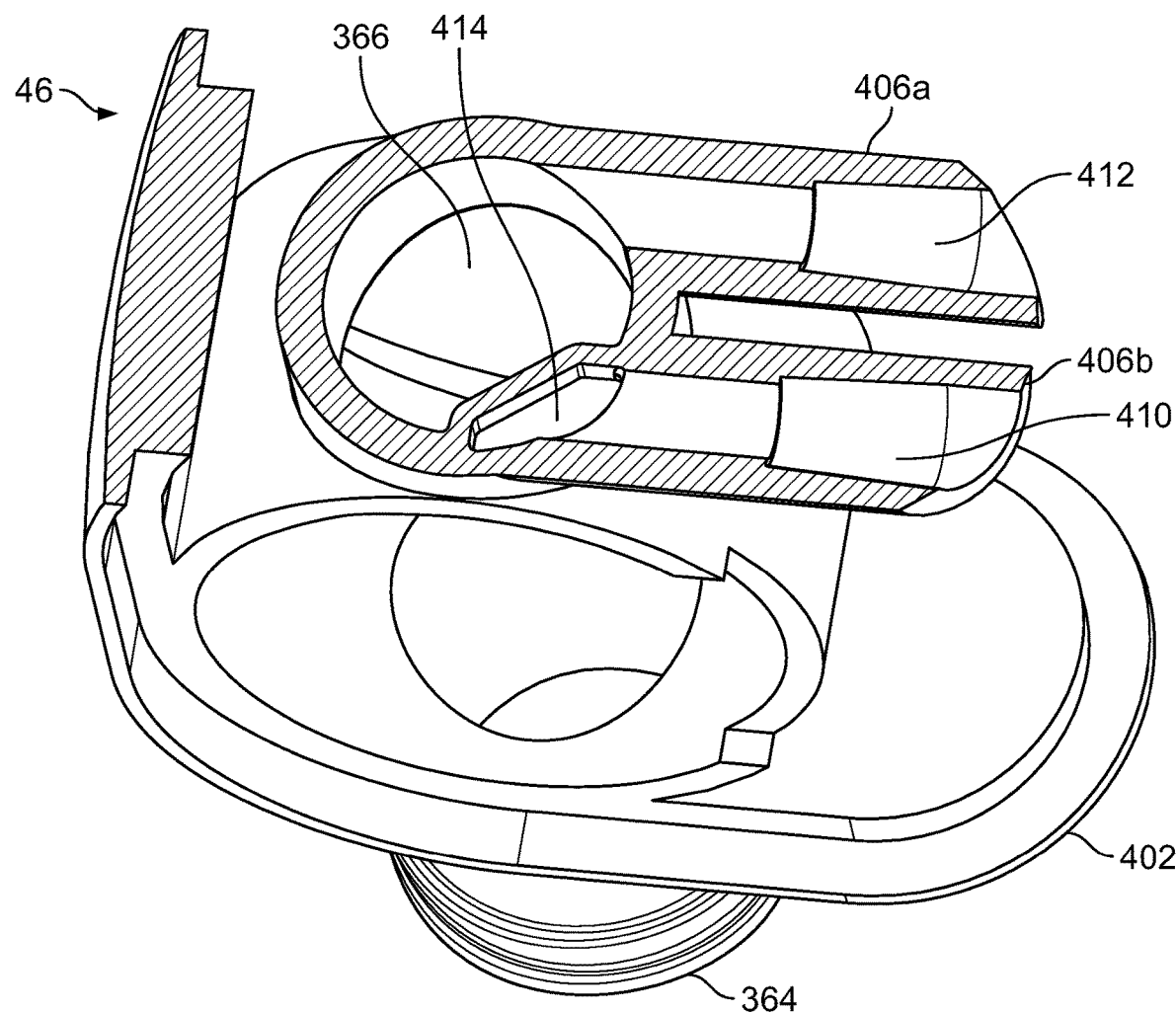
FIG. 24 is a cross sectional view of the catheter of FIG. 23 taken along lines 24-24.
Figure 25:
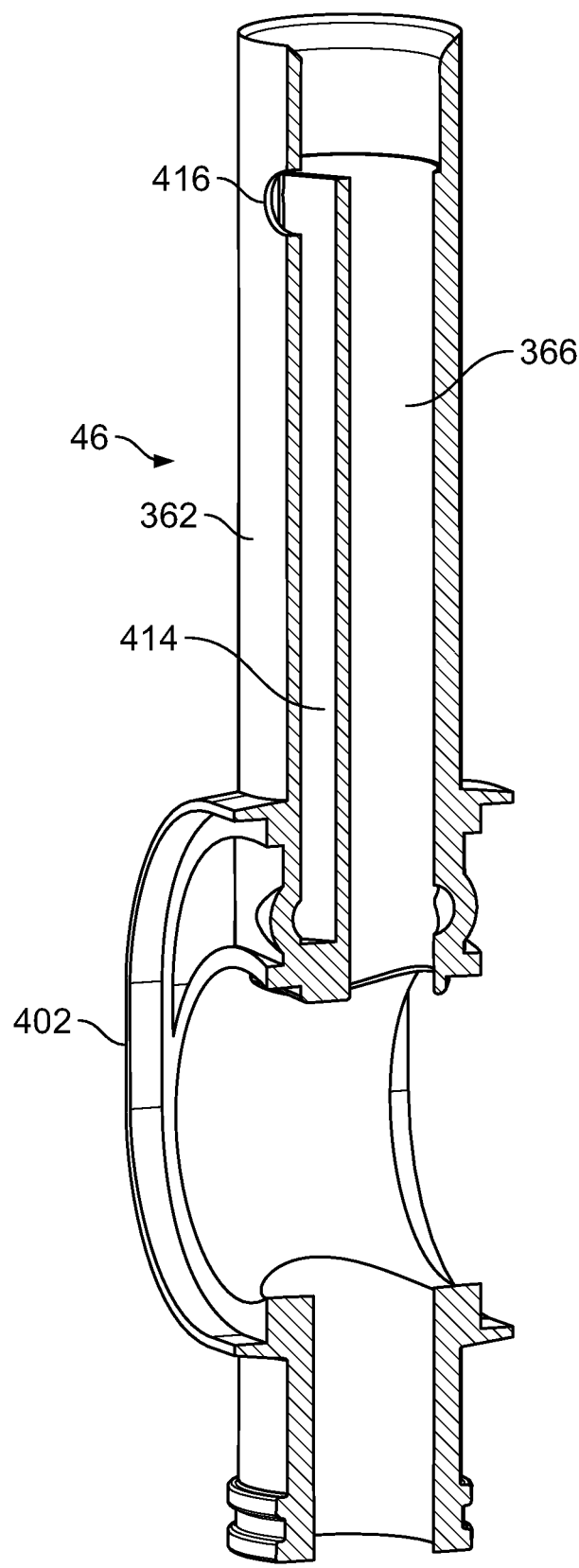
FIG. 25 is a cross sectional view of the catheter of FIG. 23 taken along lines 25-25.

Turning to FIG. 23, the base 312 of catheter 46 includes a housing 402 having a housing cover 404. Positioned within the housing are a flushing fluid stem 406a and balloon inflation fluid stem 406b. As shown in FIG. 24, the balloon inflation stem 406b contains a balloon inflation duct 410 while the flushing fluid stem 406a contains a flushing fluid duct 412. The flushing fluid duct 412 is in fluid communication with upper drain passage 366 (FIGS. 20A, 20B and 25) of the catheter upper stem 362. In embodiments where separate flushing and drain passages are used, the flushing fluid duct is in communication with the dedicated flushing fluid duct, such as a separate duct formed in the upper stem of the catheter (366a of FIG. 26) or tubing that traverses the upper drain passage. The balloon inflation duct is in fluid communication with a balloon inflation lumen 414 (FIGS. 24 and 25) formed in catheter upper stem 362 that features an orifice 416. In an alternative embodiment, the balloon inflation lumen may take the form of tubing with a first end that connects to the balloon inflation duct and passes through the upper waste drain passage of the catheter. The second end of the tubing connects to the orifice 416 so that it may communicate with the interior of the retention balloon.

With reference to FIGS. 1 and 23, tubing 54a is attached to flushing fluid stem 406a and tubing 54b is attached to balloon inflation fluid stem 406b.

As shown in FIGS. 19A and 19B, the top of the catheter upper stem features a tapered head 418 featuring openings 422 through which flushing liquid and waste may pass. As is known in the art, such members are preferably formed from a semi-rigid material such as silicon or rubber. In addition, an annular, inflatable retention balloon 424 is positioned upon the catheter upper stem 362 and has an interior that is in fluid communication with orifice 416 (FIG. 25) of the balloon inflation lumen 414.

A simplified illustration of the system 40 of FIG. 1 is presented in FIG. 26 with the components described above illustrated in schematic form. In the illustration of FIG. 26, the upper drain passage 366 of FIGS. 20A, 20B, 24 and 25 is divided into a flushing passage 366a and a drain passage 366b for ease of illustration and as illustration of an alternative embodiment of the catheter. As noted above with reference to FIGS. 7 and 12, the controller includes an indicator wheel 224 that is positioned below a window 226 formed in control panel 164. The indicator wheel includes setting icons 228 that appear in the control panel window based on the setting of valve mechanisms 116a-116c (FIG. 7), as directed by the manipulation of the toggle switch 156. The setting icons 228 of the controller indicator wheel are presented in FIGS. 27 (in the left-most column) and 28A-28E.

FIGS. 26-28E will now be used to describe operation of the system 40 in performing TAI.

Stage One: Priming of the System Tubing and Catheter

Figure 28A:
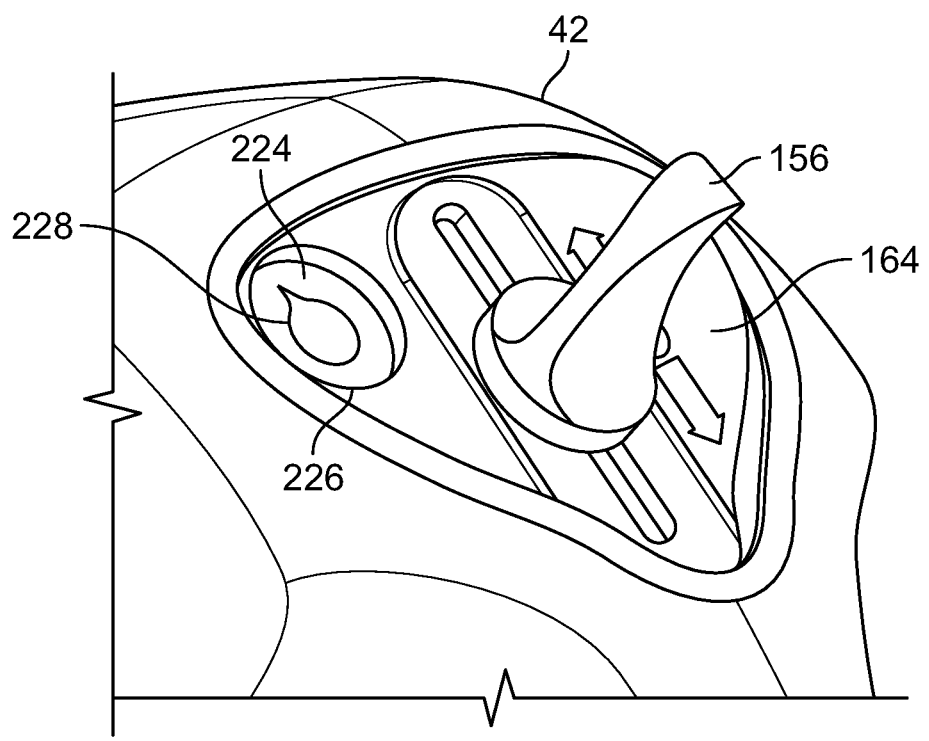
FIGS. 28A-28E illustrate use of the controller to select valve configurations.

Before the top end of the catheter, including the tapered head 418 and retention balloon 424 (FIGS. 19A and 19B), are inserted into the rectum of the user/patient, the system tubing needs to be primed in order to remove the air. To accomplish this, the user selects the "Prime" icon on the manual hand controller, as illustrated in FIG. 28a. More specifically, the user manipulates the toggle switch 156 by moving it in either direction indicated by arrows 158 (FIG. 7) until the icon of FIG. 28a appears in the control panel window 226. With reference to FIGS. 10-12, this causes the pawls 192a and 192b of the toggle mechanism to rotate ratchet wheels 208a and 208b and thus turn the shaft 202 and gears 204a, 204b and 204c. Gears 204a, 204b and 204c turn valve gears 142a, 142b and 142c (FIG. 7) and are configured so that the valves 116a, 116b and 116c are placed into the positions shown in the first row of the table of FIG. 27. As a result, with reference to FIG. 26, reservoir valve 116c (Valve 1) and flushing valve 116a (Valve 2) are open and balloon valve 116b (Valve 3) is closed. The reservoir 44 is thus placed in fluid communication with the pump bellows 84 and the pump bellows 84 is placed in fluid communication with the catheter flushing passage 366a.

Due to the flow direction orientation of the reservoir barrel check valve 116c and fixed check valve 114 (FIGS. 5 and 26), water from the reservoir is only capable of flowing from the reservoir, through the controller pump and out through the top of the catheter. As a result, when the user squeezes the controller lever (76 of FIG. 5), so as to actuate the pump bellows (84 of FIGS. 5 and 26), water exits out of the catheter flushing passage 366*a*, and thus through catheter head openings 422 (FIGS. 19A and 19B) denoting that the tubing and catheter have been primed.

The waste drain valve 313 remains in the closed configuration until opened as described below.

Stage Two: Rectal Catheter Balloon Inflation

Figure 28B:
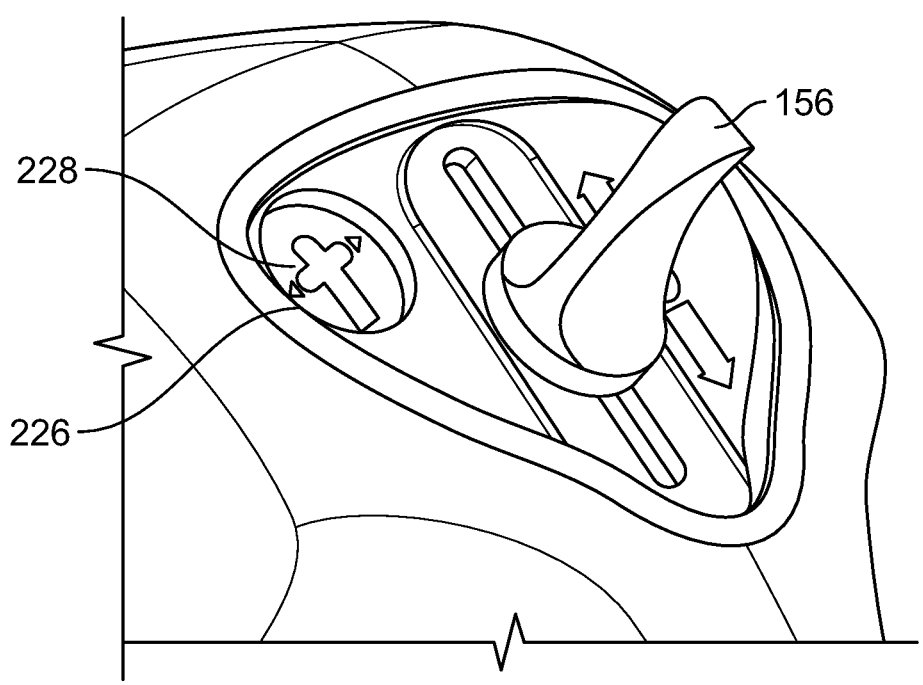

With the catheter tubing primed, the tapered head 418 and deflated retention balloon 424 (FIGS. 19A and 19B) of the catheter are safely inserted into the rectum of the user/patient. The user next toggles switch 156 of the controller until the "Balloon Inflate" icon appears in the control panel window 226, as illustrated in FIG. 28B. Due to the action of the toggle mechanism and valve assembly described above, this causes the valves 116*a*, 116*b* and 116*c* to be moved into the positions illustrated in the second row of FIG. 27. As a result, with reference to FIG. 26, reservoir valve 116*c* (Valve 1) and balloon valve 116*b* (Valve 2) are open and flushing valve 116*a* (Valve 2) is closed. The reservoir 44 is thus placed in fluid communication with the pump bellows 84 and the pump bellows 84 is placed in fluid communication with the balloon inflation lumen 414 of the catheter.

Due to the flow direction orientation of the reservoir and balloon barrel check valves 116*c* and 116*b*, water from the reservoir is only capable of flowing from the reservoir, through the controller pump and to the retention balloon 424. As a result, when the user squeezes the controller lever (76 of FIG. 5), so as to actuate the pump bellows (84 of FIGS. 5 and 26), water enters the retention balloon so as to inflate it.

Stage Three: Transfer of Irrigation Liquid from the Reservoir to the Rectum

Figure 28C:
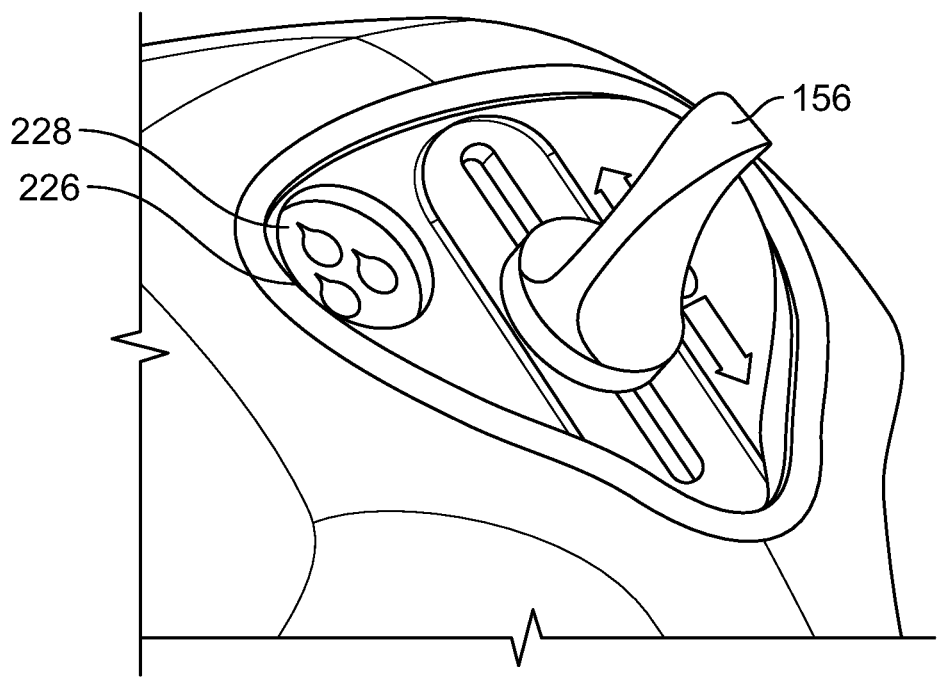

With the retention balloon of the catheter inflated, the user is now ready to irrigate the rectum. The user toggles switch 156 of the controller until the "Irrigate" icon appears in the control panel window 226, as illustrated in FIG. 28C. Due to the action of the toggle mechanism and valve assembly described above, this causes the valves 116*a*, 116*b* and 116*c* to be moved into the positions illustrated in the third row of FIG. 27. As a result, with reference to FIG. 26, reservoir valve 116*c* (Valve 1) and flushing 116*a* (Valve 2) are open and balloon valve 116*b* (Valve 3) is closed. The reservoir 44 is thus placed in fluid communication with the pump bellows 84 and the pump bellows 84 is placed in fluid communication with the catheter flushing passage 366*a*.

Due to the flow direction orientation of the reservoir barrel check valve 116*c* and fixed check valve 114, water from the reservoir is only capable of flowing from the reservoir to the catheter flushing passage. As a result, when the user squeezes the controller lever (76 of FIG. 5), so as to actuate the pump bellows (84 of FIGS. 5 and 26), water flows through the flushing passage of the catheter and into the rectum of the patient.

As an example only, each squeeze of the lever may transfer 100*m*L of water into the rectum. Consequently, water will pass through the catheter lumen, out through the openings 422 (FIGS. 19A and 19B) of the tapered head 418 of the catheter and irrigate the rectum. Fixed check valve 114 prevents any fecal or other waste matter from contaminating the irrigation tubing and water reservoir.

Stage Four: Opening the Waste Drain Valve

Figure 28D:
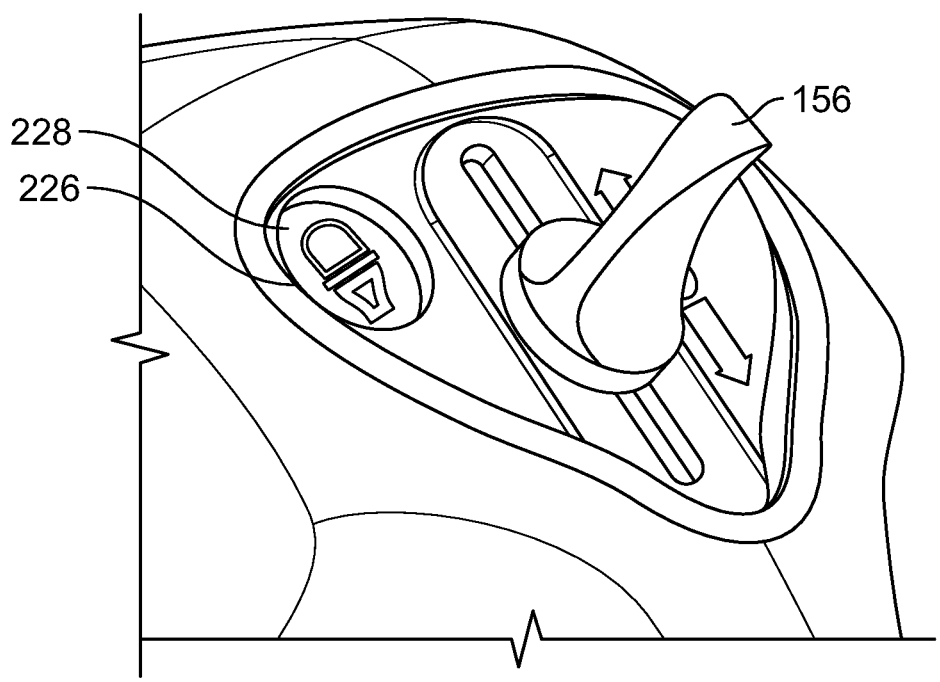

After the appropriate volume of water has been introduced into the rectum, it shall be allowed to irrigate the rectum for a defined period of time. Thereafter, the user performs two actions. First, the user toggles switch 156 of the controller until the "Flush" icon appears in the control panel window 226, as illustrated in FIG. 28D. Due to the action of the toggle mechanism and valve assembly described above, this causes the valves 116*a*, 116*b* and 116*c* to be moved into the positions illustrated in the fourth row of FIG. 27. As a result, with reference to FIG. 26, valves 116*c* (Valve 1) and 116*a* (Valve 2) and valve 116*b* (Valve 3) are all closed.

As the second action, the catheter waste drain valve 313 must be opened. As described previously with reference to FIGS. 1 and 6, the head portion of the controller is provided with sliding switches 284*a* and 284*b*, which have the resting positions illustrated in FIGS. 1 and 29A. As may be seen in FIG. 29A, the sliding switch 284*b* is positioned next to an icon 442 indicating a closed condition for the drain valve when in the rest position. The same graphic is provided on the opposite side of the controller head for switch 284*a*. To open the catheter waste drain valve, the user moves sliding switches 284*a* and 284*b* forward in the direction of arrow 447 and towards the "open waste drain valve" icon 445, as illustrated in FIG. 29B. As a result, with reference to FIG. 6, the carriage 272 slides forward in the direction of arrow 446 against the urging of spring 308 in spring linkage 294 (and the corresponding spring provided for the opposite side of the carriage) so that the controller internal waste drain control line 258 is pulled forward, also in the direction of arrow 446.

Line 258 passes over a horizontal guide rod (that is parallel to the toggle mechanism gear shaft 202 of FIGS. 11 and 12) and down through the controller handle, as illustrated in FIG. 13. As a result, with reference to FIG. 13, the portion of line 258 in the handle of the controller is pulled generally upwardly causing latching member 256 to slide up along guide rod 254. With reference to FIGS. 18 and 14, latching member 256 pulls the hook portion 262 of sliding connector 238 upwardly with it, which causes the drain valve control line 248 of FIG. 15B to also be pulled upwardly and into the tubing and drain valve control line connector housing. Waste drain valve control line 248 of FIG. 15B, as noted previously, is housed within the sheath 56 of FIG. 1 and, as illustrated in FIGS. 18A and 18B, travels into the housing of hub 48.

Line 248 is pulled in the direction of arrow 452 of FIG. 19A and, as a result, the motion converter 342 is slid into the position illustrated in FIG. 19B (against the urging of spring 348). This causes the hub pivoting disk 324*a* and 324*b* (FIG. 21) to be rotated so that the barrel valve member 314 of the waste drain valve is moved into the position illustrated in FIGS. 18B and 20B so as to open the catheter waste drain valve 313 (FIG. 26). As a result, the liquefied fecal and other waste flows into the openings 422 of the catheter through upper and lower catheter drain passages 366 and 368 (FIG. 20B) or the dedicated drain passage 366*b* of FIG. 26, and exits into a toilet, waste collection bag or other waste disposal destination or device.

Figure 29A:
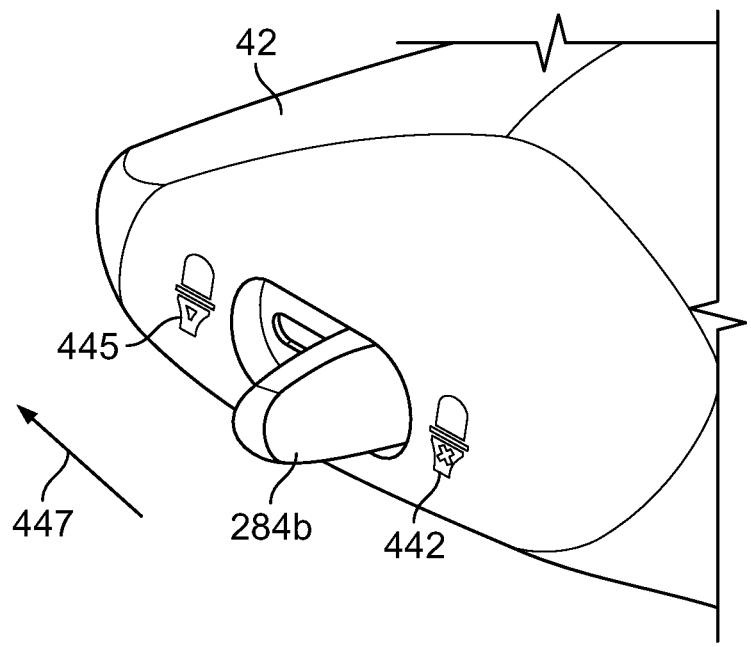
FIGS. 29A and 29B illustrate the controller slide switch for controlling the catheter drain valve in positions corresponding to a closed drain valve and an open drain valve, respectively.
Figure 29B:
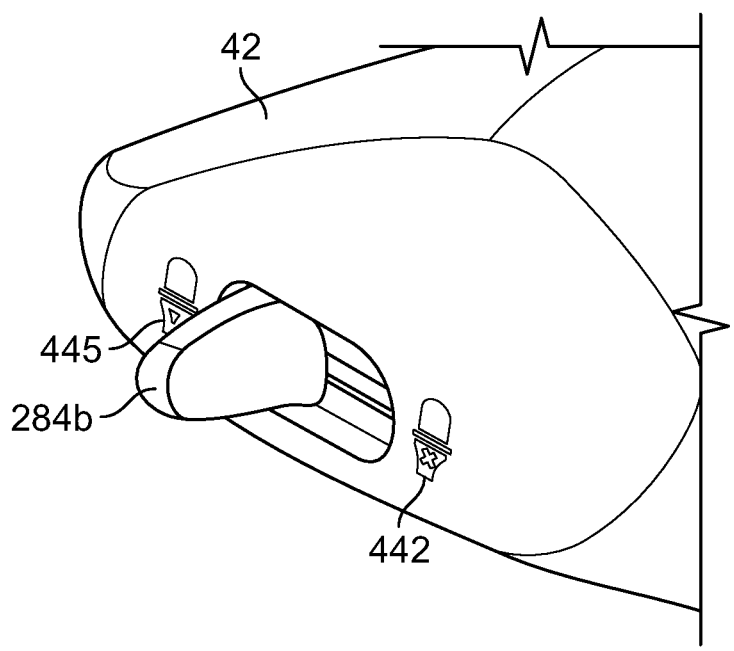

Once the patient's rectum has been emptied of the liquefied stool, the waste control valve is closed by the user releasing the slide switches 284*a* (FIG. 6) and 284*b* (FIGS. 29A and 29B). The carriage spring mechanism 294 of FIG. 6 (and the corresponding spring mechanism provided for the opposite side of the carriage) causes the switches 284*a* and 284*b* to move back into the position illustrated for switch 284*b* in FIGS. 29BA and 1. With the tension released from line 258 (FIGS. 6 and 13) and thus line 248 (FIGS. 18A-19B), spring 348 (FIGS. 19A and 19B) of the catheter hub forces the motion converter 342 back into the position illustrated in FIG. 19A so that the catheter waste drain valve is closed.

Stage Five: Repeat Irrigating the Rectum

In some TAI procedures, it may be desirable to repeat irrigation of the rectum so that steps three and four described above are repeated. More specifically, after the controller waste drain slide switches 284*a* and 284*b* are released, the user toggles switch 156 of the controller until the "Irrigate" icon appears in the control panel window 226, as illustrated in FIG. 28C. Steps three and four above are then repeated so that the rectum is again irrigated and liquefied fecal and other waste is drained. This series of steps shall be repeated until the user is confident that they have successfully completed their TAI procedure.

Stage Six: Deflating the Rectal Catheter Balloon

Figure 28E:
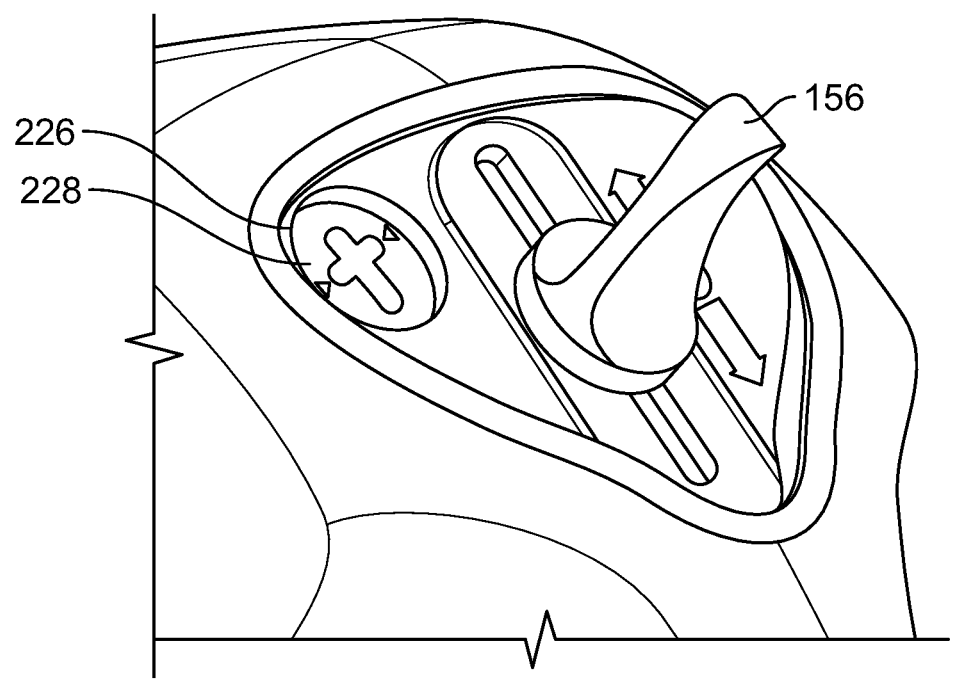

When the user is confident that they have completed their TAI procedure, the catheter needs to be removed from the rectum. Hence, the retention balloon 424 is deflated by the user toggling switch 156 until the "Balloon Deflate" icon appears in the control panel window 226, as illustrated in FIG. 28E. Due to the action of the toggle mechanism and valve assembly described above, this causes the valves 116*a*, 116*b* and 116*c* to be moved into the positions illustrated in the fifth row of FIG. 27. As a result, with reference to FIG. 26, reservoir valve 116*c* (Valve 1) and balloon valve 116*b* (Valve 3) are configured so that liquid may flow from the retention balloon 424 to the reservoir vessel 44. Flushing valve 116*a* (Valve 3) remains closed.

Due to the reversed flow direction orientation of the reservoir and balloon barrel check valves 116*c* (Valve 1) and 116*b* (Valve 3), water from the reservoir is only capable of flowing from the balloon, through the controller pump and to the reservoir. As a result, when the user squeezes the controller lever (76 of FIG. 5), so as to actuate the pump bellows (84 of FIGS. 5 and 26), water flows from the balloon through the tubing 54*b*, balloon valve 116*b* (Valve 3), the pump bellows, reservoir valve 116*c* (Valve 1) and line 52 to the reservoir 44. As a result, the retention balloon is deflated.

Once the balloon is fully deflated, the user can then safely remove the catheter from the rectum, disconnect the catheter from the hub and dispose of the catheter hygienically.

As illustrated in FIGS. 6 and 16, the head portion 68 of the controller 42 is provided with a head strap retention loop 462, while the controller handle portion 72 is provided with a handle strap retention loop 464. With reference to FIG. 16, the bottom surface 466 of the controller head portion and the front surface 468 of the controller handle portion are shaped and oriented with respect to one another to engage the upper thigh or other limb of the user. As a result, the controller may be strapped to the thigh or other limb 470 of the user using a strap 472 that passes through the head and handle strap retention loops (as shown in FIG. 16). This provides ease of use of the controller pumping lever 76, toggle switch 156 and drain valve sliding switches 284*a* and 284*b*.

It is to be understood that while valves featuring rotating valve barrel members are described for the controller valves 116*a*, 116*b* and 116*c* and for the waste drain valve 313 of the catheter, other types of valves known in the art may be used. In addition, while a bellows pump is illustrated for the controller, other types of pumps known in the art may be used. In addition, alternative switching mechanisms known in the art may be used for selecting the controller and drain valve configurations.

While the preferred embodiments of the disclosure have been shown and described, it will be apparent to those skilled in the art that changes and modifications may be made therein without departing from the spirit of the disclosure, the scope of which is defined by the following claims.

What is claimed is:

1. A system for performing irrigation of a body cavity comprising:
   a. a reservoir configured to contain an irrigation liquid;
   b. a catheter configured to be at least partially inserted into the body cavity having a flushing passage, a drain passage and a retention balloon;
   c. a waste drain valve in fluid communication with the drain passage of the catheter and movable between a closed configuration, where waste is retained within the drain passage, and an open configuration where waste flows through the drain passage;
   d. a controller in fluid communication with the reservoir and the catheter, said controller having a bellows pump and a valve assembly;
   e. the valve assembly of the controller includes:
      (i) a reservoir reversable check valve in fluid communication with the reservoir and the bellows pump, the reservoir reversible check valve having a first configuration that allows irrigation liquid to travel only from the reservoir to the bellows pump, a second configuration that allows irrigation liquid to travel only from the bellows pump to the reservoir, and a third configuration in which the reservoir reversable check valve is closed,
      (ii) a balloon reversable check valve in fluid communication with the bellows pump and the retention balloon of the catheter, the balloon reversible check valve having a first configuration that allows irrigation liquid to travel only from the bellows pump to the retention balloon, a second configuration that allows irrigation liquid to travel only from the retention balloon to the bellows pump, and a third configuration in which the balloon reversable check valve is closed, and
      (iii) a flushing valve in fluid communication with the bellows pump and the catheter,
   f. the valve assembly changeable between configurations so that when the bellows pump is actuated:
      i) irrigation liquid is drawn from the reservoir into the bellows pump and the irrigation liquid is pushed out of the bellows pump to the retention balloon when the reservoir reversable check valve is in the first configuration, the balloon reversable check valve is in the first configuration, and the flushing valve is in a closed configuration;
      ii) irrigation liquid is drawn from the reservoir into the bellows pump and is pushed out of the bellows pump to the flushing passage of the catheter when the reservoir reversable check valve is in the first configuration, the balloon reversable check valve is in the third configuration, and the flushing valve is in an open configuration; or
      iii) irrigation liquid is drawn from the retention balloon into the bellows pump and the irrigation liquid is drawn out of the bellows pump to the reservoir when the reservoir reversable check valve is in the second configuration, the balloon reversable check valve is in the second configuration, and the flushing valve is in the closed configuration.

2. The system of claim 1 wherein the controller includes a waste drain valve control switch configured to open the waste drain valve.

3. The system of claim 2 further comprising a sheath connected between the controller and the waste drain valve; and a waste drain valve control line having a first end connected to the waste drain valve control switch.

4. The system of claim 3 wherein the waste drain valve is positioned within the catheter.

5. The system of claim 4 further comprising a hub, a tubing connected to the hub, and a waste drain valve opening mechanism, wherein the hub is configured to be removably connect to the catheter, and the controller is in fluid communication with the catheter by the tubing connected to the hub and wherein a second end of the waste drain valve control line is connected to the waste drain valve opening mechanism within the hub configured to open the waste drain valve.

6. The system of claim 5 wherein the waste drain valve includes a barrel member and the waste drain valve opening mechanism within the hub includes a pivoting disk configured to turn the barrel member of the waste drain valve.

7. The system of claim 1 wherein the controller includes a head portion and a handle portion and the bellows pump is positioned within the head portion and a lever positioned on the handle portion, said lever configured to move the bellows pump between expanded and contracted configurations when the lever is actuated.

8. The system of claim 1 further comprising a hub configured to removably connect to the catheter, and further comprising the controller is in fluid communication with the catheter by tubing that connects to the hub.

9. The system of claim 1 wherein the flushing passage and an upper portion of the drain passage are combined into a single passage.

10. The system of claim 1 wherein the controller includes a toggle mechanism connected to the valve assembly and operable to reconfigure the valve assembly.

11. The system of claim 1 wherein the catheter is disposable.

* * * * *